(12) United States Patent
Jelle et al.

(10) Patent No.: US 10,695,174 B2
(45) Date of Patent: Jun. 30, 2020

(54) INSERTION TOOLS FOR MEDICAL DEVICES AND METHODS FOR USING

(71) Applicant: SURMODICS, INC., Eden Prairie, MN (US)

(72) Inventors: Bruce M. Jelle, Eden Prairie, MN (US); Joram Slager, St. Louis Park, MN (US); Joseph S. McGonigle, Minneapolis, MN (US); Rick Murphy, White Bear Township, MN (US); Andrew G. Bach, St. Louis Park, MN (US); Teryl L. Woodwick Sides, Maple Grove, MN (US); Ambereen Angamuthu, Edina, MN (US); Sean Lundquist, Chaska, MN (US); Gary Opperman, St. Louis Park, MN (US); Nathan A. Lockwood, Minneapolis, MN (US)

(73) Assignee: Surmodics, Inc., Eden Prairie, MN (US)

( * ) Notice: Subject to any disclaimer, the term of this patent is extended or adjusted under 35 U.S.C. 154(b) by 347 days.

(21) Appl. No.: 15/543,704

(22) PCT Filed: Jan. 14, 2016

(86) PCT No.: PCT/US2016/013430
§ 371 (c)(1),
(2) Date: Jul. 14, 2017

(87) PCT Pub. No.: WO2016/115361
PCT Pub. Date: Jul. 21, 2017

(65) Prior Publication Data
US 2017/0367824 A1 Dec. 28, 2017

Related U.S. Application Data

(60) Provisional application No. 62/108,256, filed on Jan. 27, 2015, provisional application No. 62/103,422, filed on Jan. 14, 2015.

(51) Int. Cl.
*A61F 2/24* (2006.01)
*A61M 25/10* (2013.01)
(Continued)

(52) U.S. Cl.
CPC ......... *A61F 2/2433* (2013.01); *A61M 25/10* (2013.01); *A61M 25/0102* (2013.01);
(Continued)

(58) Field of Classification Search
CPC . A61F 2/2433; A61M 25/10; A61M 25/0102; A61M 25/0668; A61M 25/09041; A61M 2025/0681; A61M 2025/1081
See application file for complete search history.

(56) References Cited

U.S. PATENT DOCUMENTS 5,569,294 A 10/1996 Parkola
5,911,702 A 6/1999 Romley et al.
(Continued)

FOREIGN PATENT DOCUMENTS

JP 06-66698 9/1994
JP 10-66731 3/1998
JP 2006 334222 A 12/2006

*Primary Examiner* — Erich G Herbermann
(74) *Attorney, Agent, or Firm* — Kagan Binder, PLLC

(57) ABSTRACT

The disclosure provides insertion tools and articles that facilitate entry of a medical device, such as a balloon catheter, into the body. In embodiments the insertion tools have an elongate hollow body (50) that is able to protect a portion of a medical device, such as a balloon of a balloon catheter, during an insertion procedure. In one embodiment the insertion tool has an elongate hollow body (131), a tapered distal end (135), and a locking mechanism (133) at the proximal end which can secure a portion of a balloon catheter. An opening at the distal end can allow passage of the balloon in a folded uninflated state.

15 Claims, 12 Drawing Sheets

(51) Int. Cl.
    *A61M 25/06* (2006.01)
    *A61M 25/01* (2006.01)
    *A61M 25/09* (2006.01)

(52) U.S. Cl.
    CPC ... *A61M 25/0668* (2013.01); *A61M 25/09041* (2013.01); *A61M 2025/0681* (2013.01); *A61M 2025/1081* (2013.01)

(56) References Cited

U.S. PATENT DOCUMENTS

| | | | |
|---|---|---|---|
| 2004/0093005 A1* | 5/2004 | Durcan | A61M 25/00 606/194 |
| 2009/0030374 A1 | 1/2009 | Osypka | |
| 2011/0208292 A1 | 8/2011 | Von Oepen et al. | |
| 2013/0030519 A1* | 1/2013 | Tran | A61F 2/958 623/2.11 |
| 2013/0096604 A1 | 4/2013 | Hanson et al. | |

* cited by examiner

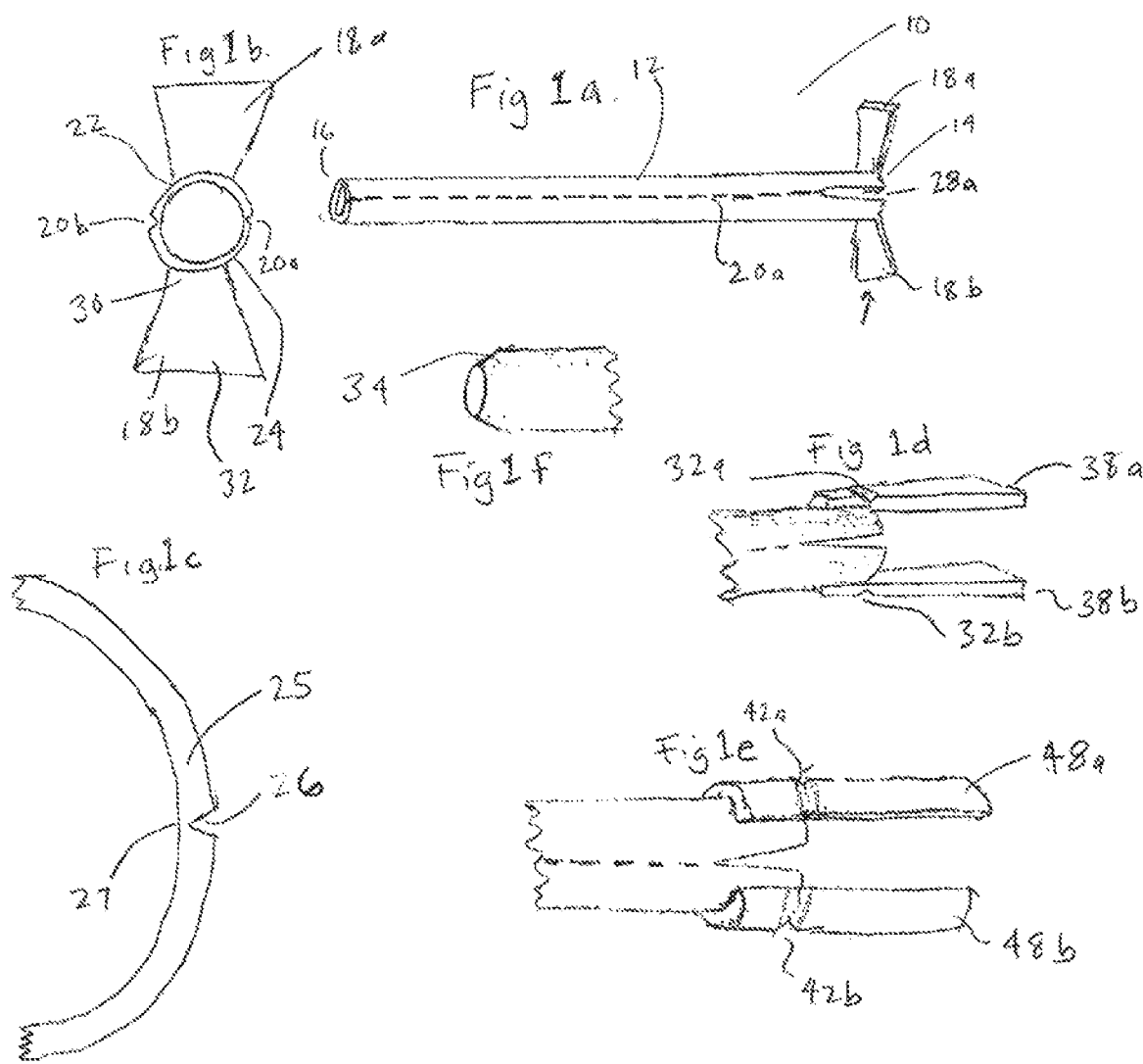

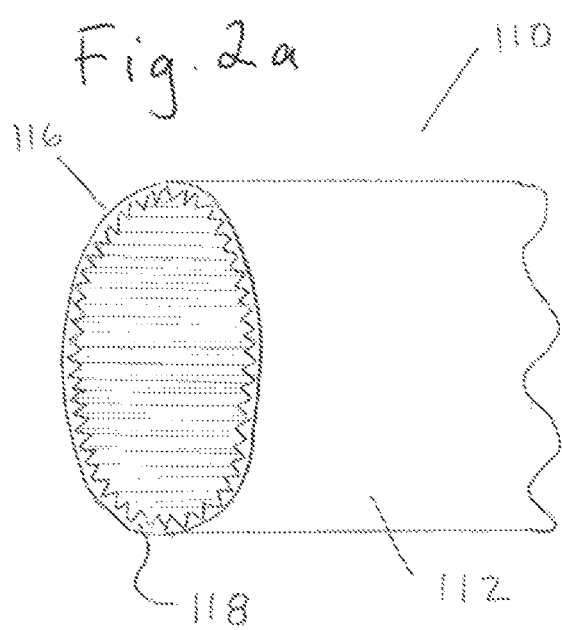
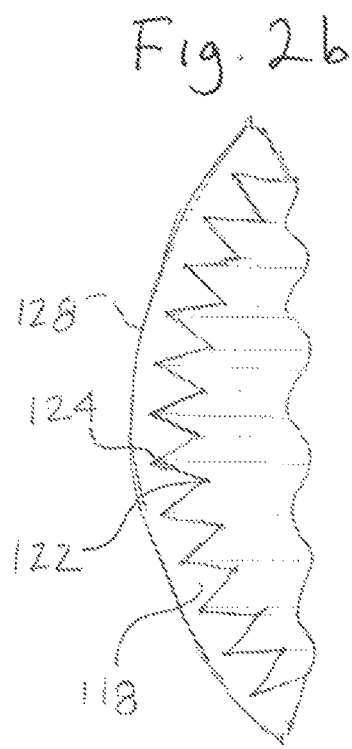
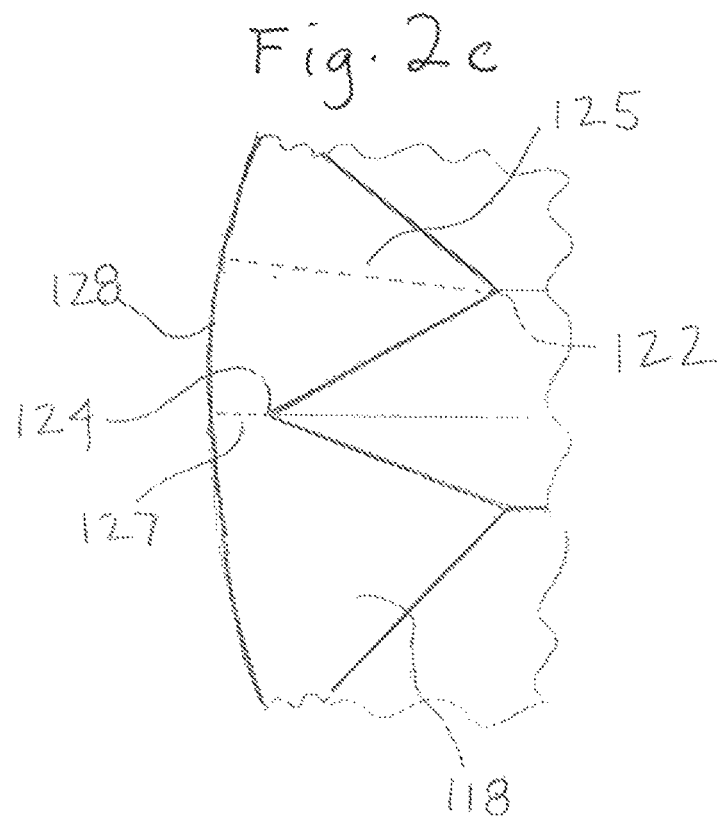

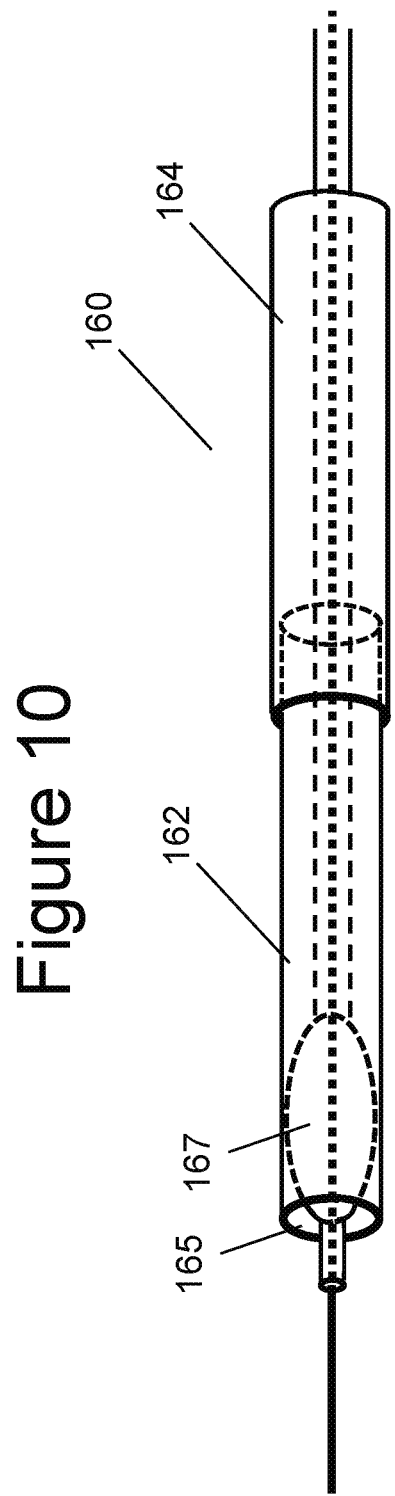

INSERTION TOOLS FOR MEDICAL DEVICES AND METHODS FOR USING

PRIORITY

The present non-provisional Application claims the benefit from International Application No. PCT/US2016/013430, filed Jan. 14, 2016, which in turn claims the benefit of commonly owned U.S. provisional Application having Ser. No. 62/103,422, filed on Jan. 14, 2015, and U.S. provisional Application having Ser. No. 62/108,256, filed on Jan. 17, 2015, both entitled INSERTION TOOL FOR MEDICAL DEVICE AND METHODS FOR USING, which Applications are incorporated herein by reference in their entireties.

FIELD

The disclosure relates to insertion tools that facilitate the insertion of a medical device into the vasculature of the body.

SUMMARY

Described herein are insertion tools and insertion articles for medical devices that are introduced into the vasculature. The insertion tools can be used for packaging and protecting an implantable or insertable medical device during storage and deployment. The insertion tools can be used to protect and facilitate the insertion of medical devices such as balloon catheters, stents, filters, shunts and the like. The insertion tool may facilitate guidewire insertion into a catheter lumen, protect the surface of a balloon member of a balloon catheter or stent during guide wire loading, provide the insertable or implantable medical device in a desired configuration prior to insertion, protect the device from contamination, and/or facilitate insertion into an access device.

The insertion tool can be a part of a kit or system used for a medical procedure, which are also embodiments of the invention. For example, the kit can include one or more of the following components: one or more delivery catheters, a balloon treatment device, an inflation catheter, a stent, a guidewire, or combinations thereof.

Insertion tools of the present disclosure can also be used to protect health care professionals from having contact with drug coatings on medical devices that are inserted into the human body. Furthermore, insertion tools can also act to protect humidity sensitive drug coatings and to avoid accidental contact with fluids with the drug coatings prior to insertion into the body of a mammal. In some situations insertion tools can also be used to aid in the placement and insertion of valves in transcatheter aortic valve replacement (TAVR) procedures.

In one embodiment, the invention provides an insertion tool for facilitating the entry of a medical device such as a balloon catheter into the body. The insertion tool includes a tubular member having a wall, and proximal and distal ends, and a length between the ends defining a first axis. In the wall of the tubular member are first and second separation margins, the margins being parallel to the first axis, opposite one another on the tubular member, and between the proximal and distal ends. The separation margins are in the form of a continuous groove or in the form of a plurality of openings in the wall of the tubular member. These separation margins can define first and second halves of the body member. Material of the tubular member is configured to fracture along the length of the margins when outward forces are applied to each half the tubular member. Also, at the proximal end of the tubular member is a first notch that is adjacent to the proximal end of the first separation margin and a second notch that is adjacent to the proximal end of the second separation margin. The notches provide starting points for the separation of the tubular member. Further, the tool includes first and second separation assist members connected to the proximal end of the tubular member and opposite one another on the tubular member, and between the first and second notches. The separation assist members can be in the form of tabs which can be pinched with fingers and then manually pulled apart. Also, the tool has a tapered distal end wherein a thickness of the wall of the tubular member is reduced in a proximal to distal direction.

In another embodiment, the invention provides an insertion tool for facilitating the entry of a medical device, such as a balloon catheter, into the body, the tool including a tubular member comprising a wall having an inner surface, an outer surface, proximal and distal ends, and a length between the ends defining a first axis. The inner surface, the outer surface, or both, of the wall comprises a plurality of ridges running parallel to the first axis and about the circumference of the inner wall. The ridges define areas of the wall having a first thickness, and between the ridges areas of the wall having a second thickness wherein the first thickness is greater than the second thickness. Material of the tubular member is configured to fracture along the length of the wall between the ridges when outward forces are applied to each half the tubular member. Also at the proximal end of the tubular member is a first notch that is adjacent to the proximal end of a first area of the of the tubular member that is between a first set of two ridges, and a second notch that is adjacent to the proximal end of a second area of the of the tubular member that is between a second set of two ridges. The tool also includes first and second separation assist members connected to the proximal end of the tubular member and opposite one another on the tubular member and between the first and second notches.

Embodiments of the invention also provide methods for delivering a medical device into a patient's body using the insertion tool embodiments of the invention. The method includes steps of (a) providing an insertion tool loaded with an implantable or insertable medical device such as a balloon catheter, and (b) moving, directly or indirectly, the insertable or implantable medical device from the insertion tool into the patient's body.

In another embodiment, the invention provides another insertion tool for facilitating the entry of a balloon catheter into the body. The tool includes a tubular member comprising outer and inner surfaces; a distal end comprising an opening and defining inner and outer diameters, wherein inner diameter is sized to allow passage of a balloon portion of a balloon catheter through the tubular member, a proximal end comprising an opening and having inner and outer surfaces defining inner and outer diameters, wherein between the proximal and distal ends the outer surface of the tubular member is sized to fit within a portion of a hemostatic valve; a length between the proximal and distal ends that is greater that a length between two openings of a hemostatic valve; a flange arranged about the outer diameter of the proximal end; wherein the inner diameter of the distal end is smaller than the inner diameter of the proximal end, thereby providing a tapered configuration to the tubular member.

In another embodiment, the invention also provides another method for introducing a balloon catheter into the body. The method comprises use of a hemostatic valve and a balloon catheter insertion tool. In the method a hemostatic valve comprising proximal and distal openings is engaged with an artery. An insertion tool is provided, the tool comprising a tubular member comprising outer and inner surfaces; a distal end comprising an opening and defining inner and outer diameters, a proximal end comprising an opening and having inner and outer surfaces defining inner and outer diameters, wherein between the proximal and distal ends the outer surface of the tubular member is sized to fit within a portion of the hemostatic valve; a length between the proximal and distal ends that is greater that a length between two openings of a hemostatic valve; a flange arranged about the outer diameter of the proximal end; wherein the inner diameter of the distal end is smaller than the inner diameter of the proximal end, thereby providing a tapered configuration to the tubular member. The distal end of the insertion tool is moved through the first and second openings of the hemostatic valve so the proximal opening of the hemostatic valve is tightened around the outer surface of the insertion tool. A balloon portion of a balloon catheter is moved through the insertion tool and into the artery.

In another embodiment, the invention provides another insertion tool for facilitating the entry of a balloon catheter into the body. The tool comprises first and second elongate members each comprising a distal portion with a distal end, the distal portion comprising an arcuate shape that provides the distal portion with a trough-like configuration; and a proximal portion comprising a tab that is at an angle to the distal portion. The first and second elongate members are connected to each other by a set of hinges that bias the distal ends towards each other, and wherein the ends can be moved apart by applying pressure to the tabs, wherein the first and second elongate members form an opening from that allows passage of a balloon catheter through the tool from the proximal to distal portions when the distal ends are moved apart from one another.

In another embodiment, the invention provides another method for introducing a balloon catheter into the body, the method comprising use of a hemostatic valve and a balloon catheter insertion tool. The method comprises steps of: providing a hemostatic valve comprising proximal and distal openings engaged with an artery; providing an insertion tool the tool comprising: first and second elongate members each comprising a distal portion with a distal end, the distal portion comprising an arcuate shape that provides the distal portion with a trough-like configuration; and a proximal portion comprising a tab that is at an angle to the distal portion; wherein the first and second elongate members are connected to each other by a set of hinges that biases the distal ends towards each other and wherein the ends can be moved apart by applying pressure to the tabs, wherein the first and second elongate members form an opening from that allows passage of a balloon catheter through the tool from the proximal and distal portions when the distal ends are moved apart; placing the distal ends of the first and second elongate members of the insertion tool in an opening of a hemostatic valve; applying pressure to the tabs to move the distal ends apart from one another to expand the opening of the hemostatic valve; and moving a balloon portion of a balloon catheter through the opening between the first and second elongate members of the insertion tool, through the hemostatic valve, and into the artery.

In an embodiment, the invention provides another insertion tool for facilitating the entry of a balloon catheter into the body. The tool includes an elongate hollow body comprising proximal and distal ends. The body is tapered at its distal end and includes an opening sized to accommodate and allow the passage of a balloon portion of a balloon catheter when the balloon portion is in a folded uninflated state. The tool includes a locking mechanism located on the proximal end of the elongate hollow body capable of securing in place a portion of the balloon catheter that is proximal to the balloon portion, to restrict movement of the balloon catheter in a proximal to distal direction.

Accordingly, the tool can be used in a method for introducing a balloon catheter into a patient's body. The method includes a step of providing the insertion tool with proximal and distal ends, tapered distal end with opening, and proximal locking mechanism, where a balloon catheter disposed and secured within the insertion tool. A balloon catheter is disposed within the elongate hollow body, with a distal tip of the balloon catheter extending distally beyond the distal end of the elongate hollow body. The balloon catheter has a balloon portion in a folded uninflated state disposed within the elongate hollow body. A portion of the balloon catheter that is proximal to the balloon portion is secured in place by the locking mechanism to restrict movement of the balloon catheter in a proximal to distal direction relative to the elongate hollow body. The elongate hollow body with secured balloon catheter is moved distally so the distal tip of the balloon catheter and the tapered distal end of the elongate body pass through an entry point in the patient's body. The locking mechanism is then unlocked to allow movement of the balloon catheter relative to the elongate hollow body. The balloon catheter is moved relative to the elongate hollow body.

In an embodiment, the invention provides another insertion tool for facilitating the entry of a balloon catheter into the body. In this embodiment, the insertion tool includes first and second elongate hollow bodies that have proximal and distal ends. The first hollow body has a proximal end with an outer diameter that is slidably movable within an inner diameter of a distal end of the second elongate member. The first hollow body also includes an opening sized to accommodate and allow the passage of a balloon portion of a balloon catheter when the balloon portion is in a folded uninflated state.

Accordingly, the tool can be used in a method for introducing a balloon catheter into a patient's body. The method includes a step of providing the insertion tool with first and second elongate hollow bodies comprising proximal and distal ends, the first hollow body having a proximal end with an outer diameter that is slidably movable within an inner diameter of a distal end of the second elongate member, wherein a balloon catheter is disposed within the first elongate hollow body. The distal end of the first elongate hollow body is introduced in the patient's body. The balloon catheter is moved distally out of the first elongate hollow body into the patient. The first elongate hollow body is moved proximally out of the patient's body. In one or more steps of the method, the first elongate hollow body is moved in relation to the second elongate hollow body.

In an embodiment, the invention provides another insertion tool for facilitating the entry of a balloon catheter into the body. In this embodiment the tool includes an elongate hollow body comprising a tapered distal end comprising an opening and two or more perforations, wherein the tapered end can be split open along the perforations to increase the size of the opening and allow for passage of a balloon catheter.

Accordingly, the tool can be used in a method for introducing a balloon catheter into a patient's body. The method includes steps of providing the insertion tool with its elongate hollow body and tapered distal end with opening and two or more perforations. The tapered distal end of the elongate hollow body is introduced in the patient's body. The tapered end is forced to be split open along the perforations to increase the size of the opening and allow for passage of a balloon catheter. The balloon catheter is moved distally out of the opening at the split distal end.

In an embodiment, the invention provides an insertion article for facilitating the entry of a balloon catheter into the body. The article includes a liquid or gel-filled tubular article that has an outer surface and an inner surface that are continuous with each other and that form a cavity. The article also has a proximal and a distal end having opening for the cavity. The article is formed from a pliable material that encompasses the liquid or gel, wherein the outer and inner surfaces are able to be moved in opposite directions while the article is stationary. The article is configured to load a balloon portion of a balloon catheter in the cavity and deliver it to an insertion site from the distal end.

Accordingly, the article can be used in a method for introducing a balloon catheter into a patient's body. The method includes providing the article loaded with a balloon catheter, introducing the distal end in a patient's body, and moving the pliable material of the outer and inner surfaces to cause the movement of the balloon catheter out of the distal end.

BRIEF DESCRIPTION OF THE DRAWINGS

FIG. 1a is an illustration of an insertion tool according to one embodiment of the disclosure.

FIG. 1b is an illustration of an end of an insertion tool according to one embodiment of the disclosure.

FIG. 1c is an illustration one half of the wall of an insertion tool according to one embodiment of the disclosure as shown from an end of the tool.

FIG. 1d is an illustration of the proximal end of an insertion tool according to one embodiment of the disclosure.

FIG. 1e is an illustration of the proximal end of an insertion tool according to one embodiment of the disclosure.

FIG. 1f is an illustration of the distal end of an insertion tool according to one embodiment of the disclosure.

FIG. 2a is an illustration of the distal end an insertion tool with inner ridges according to one embodiment of the disclosure.

FIG. 2b is an illustration of a portion of the inner surface of the distal end of an insertion tool with inner ridges according to one embodiment of the disclosure.

FIG. 2c is an illustration of a portion of the inner surface of the distal end of an insertion tool with inner ridges according to one embodiment of the disclosure.

FIG. 10 is an illustration of an insertion tool having a telescoping function of, according to one embodiment of the disclosure.

DESCRIPTION

Figure 2D:
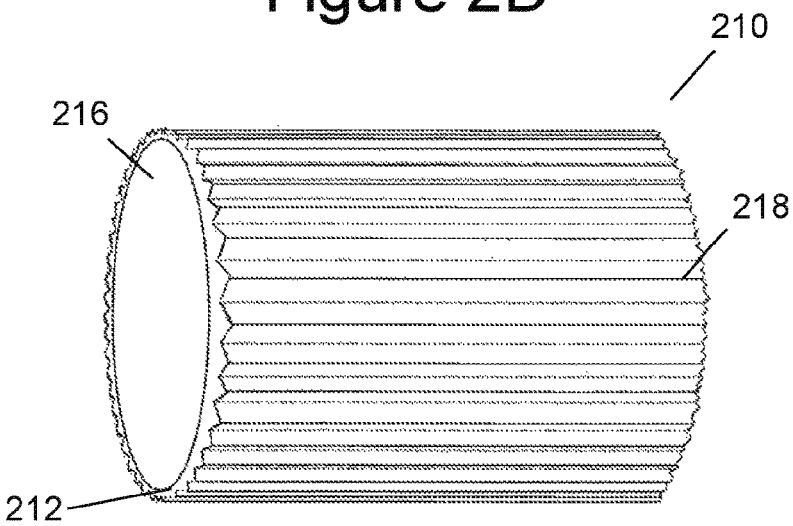
FIG. 2d is an illustration of the distal end an insertion tool with outer ridges according to one embodiment of the disclosure.

With reference to FIG. 1a, in one embodiment the disclosure provides an insertion tool 10 having a tubular member 12 having a proximal 14 and distal 16 ends. The tubular member has a first axis defining a length between the first and second ends.

Along the length of the tubular member 12 and between the proximal and distal ends are two separation margins 20a and 20b (not shown in FIG. 1a; see FIG. 1b), on opposite sides of the tubular member 12. The separation margins define first 22 and second 24 halves of the tubular member 12. For example, each half of tubular member has a semicircular shape when viewed from one end as shown in FIG. 1b.

As shown in greater detail in FIG. 1c, the separation margin can be formed by a groove 26 (or recess) in the wall of the tubular member 12. The groove causes the wall 25 of the tubular member to be thinner towards its inner surface 27. The groove 26 can be deep enough in the wall that when force is applied to separate the first 22 and second 24 halves, body member material along the separation margins fractures and the two halves of the body member separate. In some embodiments the separation margin can include perforations along its length.

Referring back to FIG. 1a, further, the tubular member can include a first notch 28a (second notch 28b hidden from view) at the proximal end of the tubular member and in line with the separation margins. The distal end of the notch 28 can meet the proximal end of the separation margin and is useful for fracturing the body member along the separation margin in a proximal to distal direction when the two halves of the body member are pulled apart at the proximal end.

As shown in FIGS. 1a, 1b, 1d, and 1f, and at or near proximal end 14 are attached to the tubular member first and second separation assist members (18a, 18b; 38a, 38b; 48a,

48*b*), which can be configured as tabs. Referring to FIG. 1*b*, the tabs can have a shape that is narrower at the point 30 were they attach to the tubular member, and are wider at their outermost edge 32. Separation assist members facilitate the process of pulling apart the halves of the tubular member when the tabs are pulled in opposite directions. The tabs can be rigid such as shown in FIGS. 1*a* and 1*b*, or can be bendable outwards and inwards, such as shown in FIGS. 1*d* and 1*e*. In order for the tabs be bendable, a groove (32*a*, 32*b*; 42*a*, 42*b*) can be present in the tab where it is attached to the proximal end of the tool.

Separation assist members may be molded together with the body member (e.g., as a unitary construction), or may be formed as independent articles and then attached to the outer surface of the body member at the proximal end with an adhesive. FIG. 1*d* shows a tab that is attached to the proximal end of the body member, and FIG. 1*e* show a tab having a partial radius to provide greater surface area contact with the outer surface of the tubular body member.

Referring to FIG. 1*f*, the insertion tool has a tapered end 34. The tapered end can be formed by reducing the thickness of the wall of tubular member in a proximal to distal direction. The tubular member 12 can have a constant inner diameter from the proximal to distal end.

In another embodiment, with reference to FIG. 2*a*, an insertion tool 110 having a tubular member 112 is formed from a wall having an inner surface, wherein the inner surface includes a plurality of ridges 118. The ridges can run the length of the tubular member 112, from its proximal 114 (not shown) to distal 116 end. In a related embodiment, with reference to FIG. 2*d*, an insertion tool 210 includes a tubular member 212 formed from a wall having an outer surface that includes a plurality of ridges 218. The ridges can run the length of the tubular member 212, from its proximal 214 (not shown) to distal 216 end. Alternatively ridges 218 can be strategically placed along the tubular member 212 where contact with an insertable medical is anticipated, for example, at tapered portions of the tubular member 212.

Figure 2E:
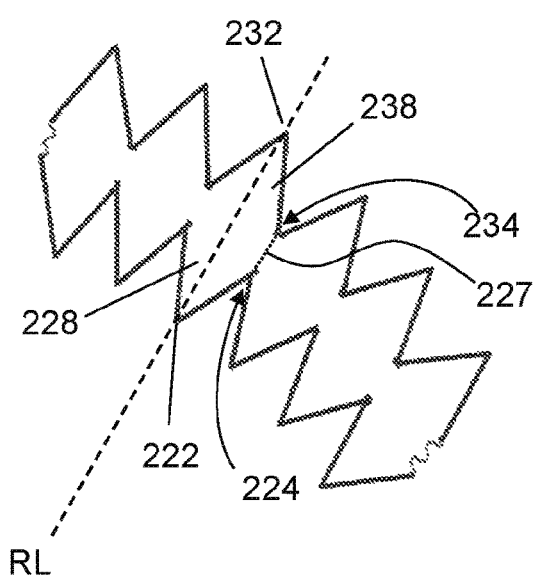
FIG. 2e is an illustration of a cross section of portion of a wall with inner and outer ridges according to one embodiment of the disclosure.
Figure 2F:
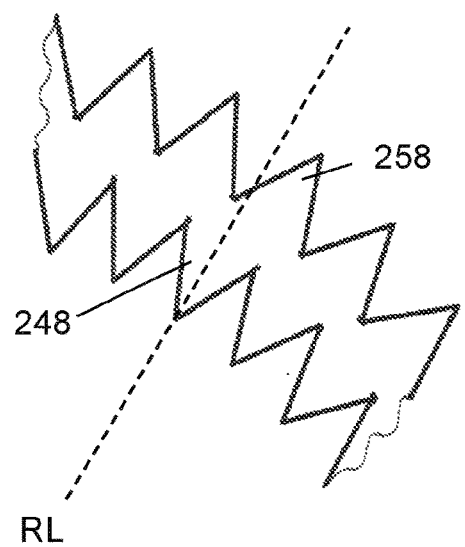
FIG. 2f is an illustration of a cross section of a portion of a wall with inner and outer ridges according to one embodiment of the disclosure.

As shown in greater detail in FIGS. 2*b* and 2*c*, the ridges 118 can define areas of the wall having a first thickness, wherein the first thickness is represented by dashed line 125. The first thickness can be the distance from the peak 122 (which may also be referred to as an "apex" or "tip") of a ridge 118 to the outer surface 128 of the wall of the tubular member 112, which can represent the thickest portion of the wall. Between the ridges are areas of the wall having a second thickness, which is the distance from the base 124 between the ridges to the outer surface 128 of the wall of the tubular member 112, and represented by dashed line 127. This second thickness can represent the thinnest portions of the wall. These parameters can also be understood for the embodiments as shown in FIGS. 2*d*-2*f*.

The first thickness is greater than the second thickness, and therefore less material of the wall is present between the base and the outer surface of the tubular member. Because the material of the wall is thin between the ridges, it allows the tubular member to be fractured along the length of the wall between the ridges when outward forces are applied to each half of the tubular member.

In some aspects, a relationship between the first thickness and the second thickness (e.g., lengths 125 and 127) can be defined by a ratio between the two. For example, an exemplary ratio of thickness can be in the range of about 10:1 (first thickness:second thickness) to about 1:2, or about 5:1 to about 1:1, such as about 2:1 in an exemplary embodiment. Increasing the ratio of thickness (first thickness:second thickness) may increase the "fracturability" of the material between the ridges, allowing the tubular member to be readily split when outward forces are applied to each half the tubular member. These parameters can also be applied to the embodiments as shown in FIGS. 2*d*-2*f*.

On the inner surface of the walls, the ridges can be configured to have any suitable shape. For example, as shown in the FIGS. 2*a*-*c*, the ridges can have an "upside-down V" shape, with the point of the "V" representing the peak 122. However, as an alternative to a pointed shape at the peak of the ridge, the peak can be rounded or flat. For example, the ridges can have an "upside-down U" shape. These shapes can also be present in the embodiments as shown in FIGS. 2*d*-2*f*.

The inner surface can include a desired number of ridges about the circumference of its inner surface. The number of ridges that are present around the circumference can be determined by various factors, such as the shape and configuration of the ridges, the first and second thicknesses, the inner diameter of the tubular member, and the desired spacing between the ridges. In some configurations, the ridges are adjacent to one another, such as shown in FIGS. 2*a*-*c*. Alternatively, the spacing between the ridges can be greater so the area of the thinner portions of the wall (second thickness) of the tubular member is increased. These shapes and arrangements can also be present in the embodiments as shown in FIGS. 2*d*-2*f*.

The configuration of the inner surface of the tubular member can also be of benefit as it reduces the area of contact between the inner wall and the surface of a medical device that is movable within the member. That is, the peaks 122 of the ridges are the only areas of the inner surface that contact the surface of the medical device which in turn minimizes any frictional effect on the surface of the medical device that is caused by the inner surface.

In some embodiments, the insertion tool has a tubular member that includes a plurality of ridges on both the inner and outer surfaces of the tubular member. FIG. 2*e* illustrates a portion of the wall of the tubular member having inner ridges 228 and outer ridges 238. A tubular member with inner 228 and outer ridges 238 can be constructed so their peaks (inner peak 222 and outer peak 232) are substantially or fully radially aligned with each other (i.e., the ridges fall along the same radial line RL emanating from the center of the tubular member). Inner and outer ridges may be aligned over a portion of the circumference of the tubular member, or over the entire circumference of the tubular member. When a series of inner and outer ridges are radially aligned with each other, the inner ridges may have smaller dimensions, as the circumference defined by the inner base points is smaller than the circumference defined by the outer base points. Accordingly, the distance between two base points defining an inner ridge can be less than the distance between two base points defining an outer ridge. Between the inner 228 and outer ridges 238 are areas of the wall having a thickness, which is the distance from the inner base 224 to the outer base 234, and represented by dashed line 227. The tubular member may be easily fractured along dashed line 227 when outward forces are applied to each half the tubular member given the minimal thickness of the wall at this location.

Figure 2G:
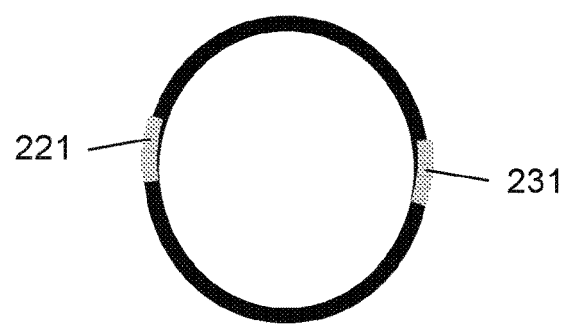
FIG. 2g is an illustration of a cross section a wall according to one embodiment of the disclosure.

In other embodiments and with reference to FIG. 2*f*, inner ridges 248 and outer ridges 258 are not radially aligned with each other over at least a portion of the circumference of the tubular member. In yet other embodiments, the insertion tool has a tubular member that includes one or more groups of ridges on both the inner and outer surfaces of the tubular member that are radially aligned with each other, and also one or more groups of ridges on both the inner and outer surfaces of the tubular member that are not radially aligned with each other. For example, and with reference to FIG. 2g, the tubular member can include two groups of ridges (group 221 and group 231) that are aligned with each other wherein these groups are on opposite sides of the tubular member, and the remaining inner and outer ridges between group 221 and group 231 are not aligned with each other. In this arrangement the wall thickness in the area defined by groups 221 and 231 can be less than the wall thickness in the areas outside these groups, and when outward forces are applied to each half the tubular member is more likely to fracture in the area defined by groups 221 and 231.

The insertion tool 110 with a plurality of ridges 118 can also include and at or near it proximal end (not shown) first and second separation assist members (such as shown with reference to FIGS. 1*a*, 1*b*, 1*d*, and 1*e*, elements 18*a*, 18*b*; 38*a*, 38*b*; 48*a*, 48*b*), which can be configured as tabs. An insertion tool 110 with a plurality of ridges 118 can also include at its proximal end notches useful for fracturing the body member along the lines of the body member between the ridges, such as shown with reference to FIG. 1*a*, elements 28*a* and 28*b*).

Figure 3A:
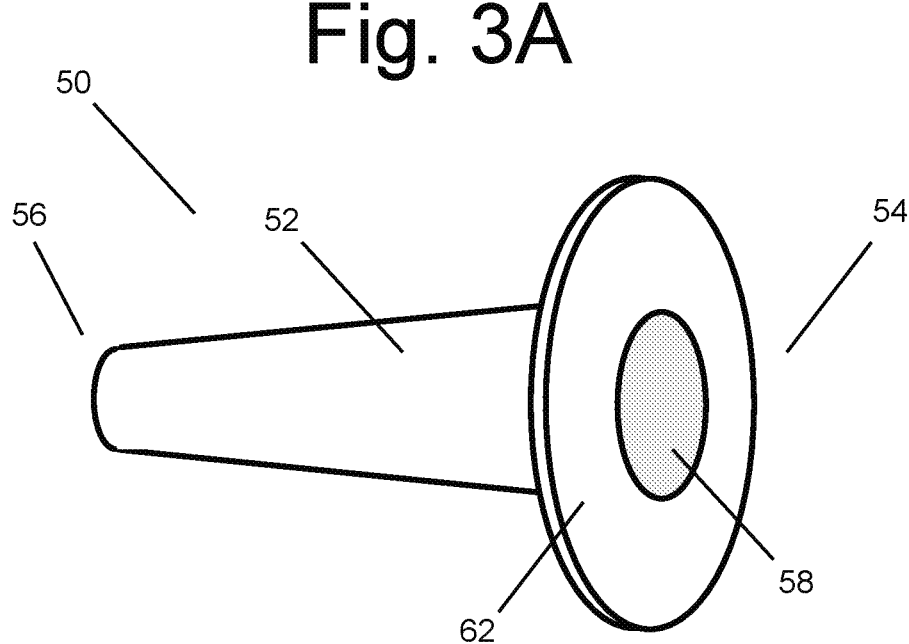
FIG. 3a is an illustration of an insertion tool according to one embodiment of the disclosure showing its proximal end.
Figure 3B:
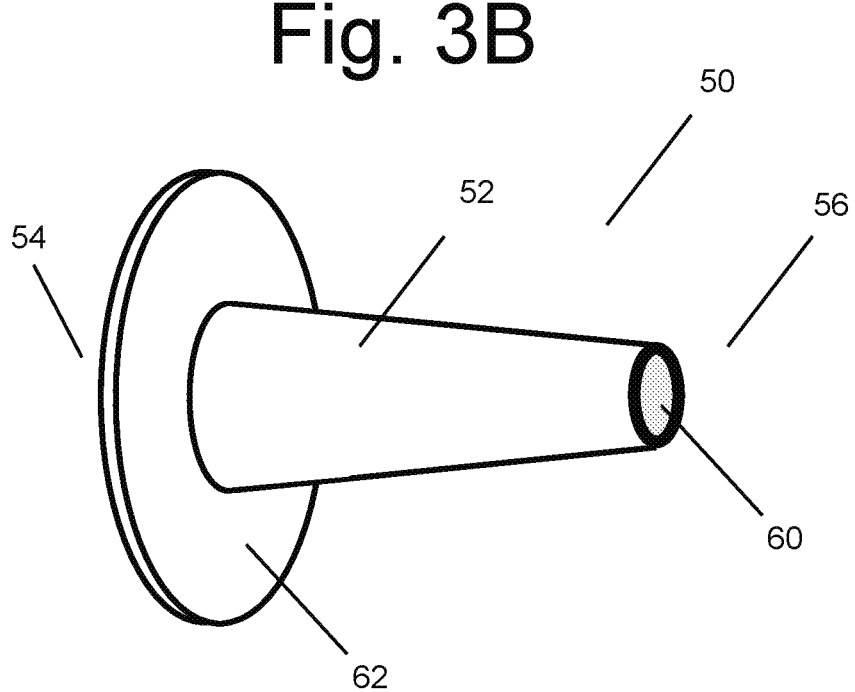
FIG. 3b is an illustration of an insertion tool according to one embodiment of the disclosure showing it distal end.

With reference to FIGS. 3*a* and 3*b*, and in another embodiment, the disclosure provides an insertion tool 50 having a tubular member 52 having a proximal end 54 and a distal end 56, with openings 58 and 60, respectively. Distal opening 60 has an inner diameter of a size sufficient to allow a balloon portion of a balloon catheter to move through it. For example, in embodiments the inner diameter at the distal opening can be at least about 2.25 mm, such as in the range of about 2.5 mm to about 7.5 mm, or about 3 mm to about 6 mm. The tubular member can define a central axis CA along the length of the member from the proximal to distal end.

Proximal opening 58 has an inner diameter that is larger than the inner diameter of the distal opening 60. For example, in embodiments the inner diameter at the proximal opening can be at least about 3 mm, such as in the range of about 3.5 mm to about 10 mm, or about 4 mm to about 8 mm.

The insertion tool also includes a flange 62 arranged about the outer diameter of the proximal end. The flange can be in the form of a circular rim, which can be at an angle to the central axis CA of the tubular member, such in the range of about 75° to about 105° the central axis, preferably about 90° to the central axis. The flange may have a diameter measured relative to the outer diameter of the proximal end of the tube, such as a diameter that is in the range of about 1.1× to about 3× the outer diameter of the proximal end of the tubular member, such a in the range of about 1.5× to about 2.5×.

Since the distal opening is smaller than the proximal opening, this provides the tubular member with a tapered configuration. Further, the along with the tapered configuration, the presence of the flange 62 arranged about the outer diameter of the proximal end provides the insertion tool with a "cone" shape.

Figure 4:
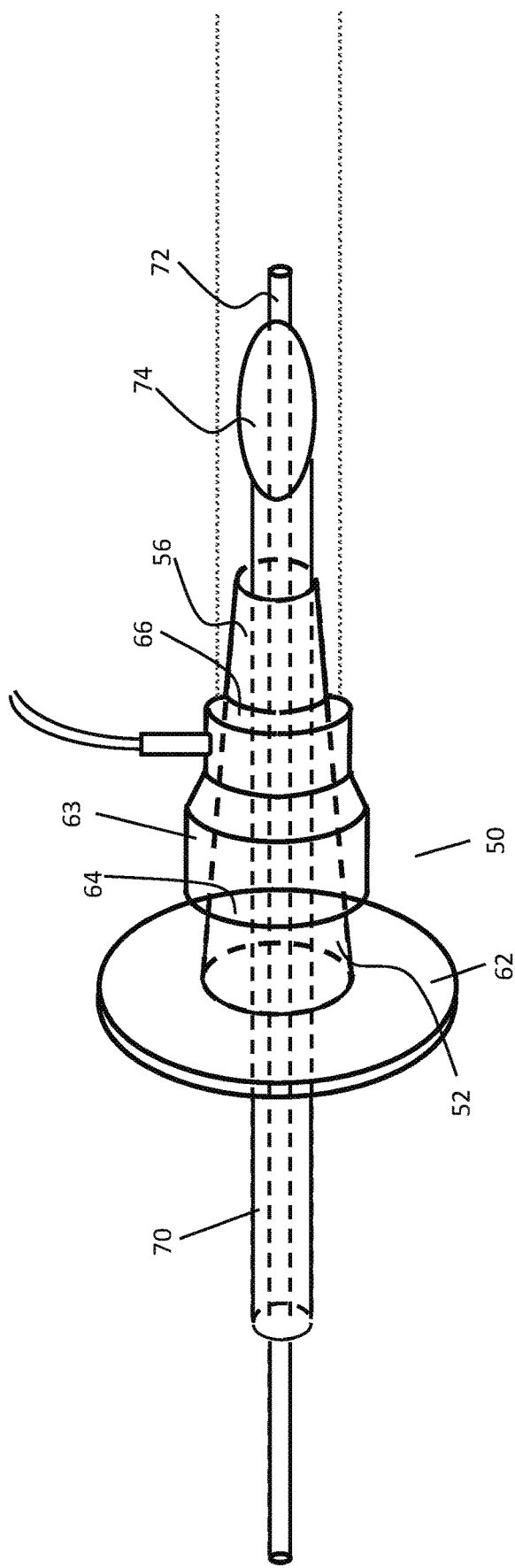
FIG. 4 is an illustration of an insertion tool according to one embodiment of the disclosure, engaged with a hemostatic valve and a portion of a balloon catheter.

In use, and with reference to FIG. 4, the insertion tool can be used in conjunction with a hemostatic valve to facilitate the entry of a balloon catheter into an artery. The hemostatic valve 63 can have a proximal 64 and distal 66 openings, the distal opening adapted to enter an artery. The distal end of the insertion tool 50 is moved into the proximal opening 64 of the hemostatic valve and out its distal opening 66, so the distal end 56 of the insertion tool 50 is within the artery. The flange 62 of the insertion tool 50 can be held between two fingers and therefore useful for moving the insertion tool in and out of the hemostatic valve. As the tubular member 52 of the insertion tool 50 increases in diameter towards its proximal end 54, it engages and seals with the inner surface of the hemostatic valve 63, generally near or at the proximal end 54 of the insertion tool. The flange 62 can also serve as a stop to the proximal movement of the tubular member 52 in the hemostatic valve 63, where the distal face 61 of the flange 62 may abut the proximal face of the hemostatic valve 63.

A balloon catheter 70 can be moved through the insertion tool 50 which facilitates its entry into an artery. In one mode of practice, the balloon end 72 of the balloon catheter 70 can be placed within the insertion tool prior to attachment to the hemostatic valve 63, and then the distal end 56 of the insertion tool, along with the balloon portion 74 of the balloon catheter 70, can be moved into the hemostatic valve 63. After the insertion tool is sufficiently engaged with the hemostatic valve the balloon catheter can be advanced to move it into the artery to a treatment site.

In another mode of practice, the insertion tool 50 is first attached to the hemostatic valve 63 prior to introducing the balloon catheter 70. For example, the distal end 56 of the insertion tool, without the balloon catheter 70, can be moved into and sufficiently engaged with the hemostatic valve 63. Next, the balloon end 72 of the balloon catheter 70 can be placed within the insertion tool 50 that is engaged with the hemostatic valve 63 and then advanced through the insertion tool 50 to an artery to a treatment site.

Figure 5:
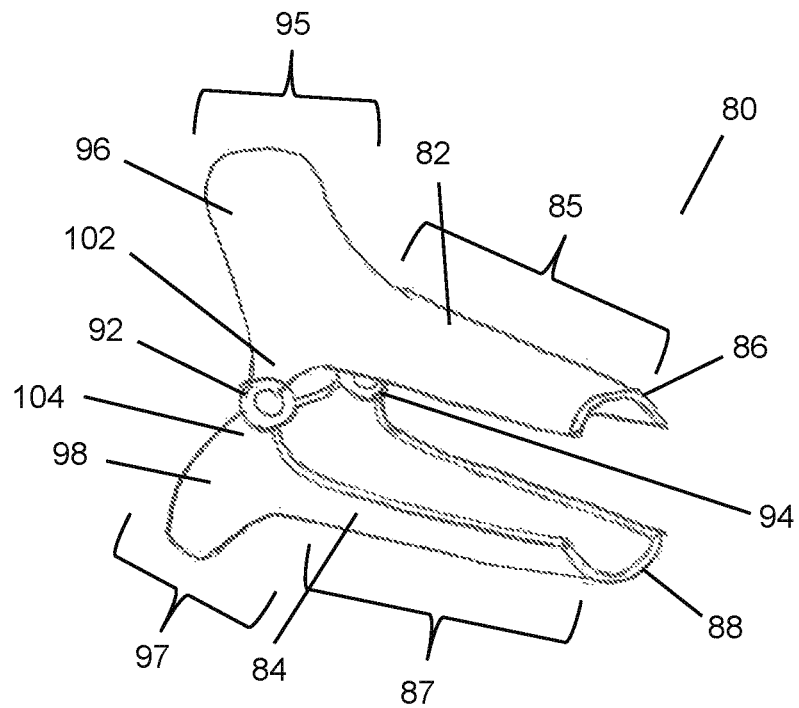
FIG. 5 is an illustration of an insertion tool according to one embodiment of the disclosure showing its distal end.

With reference to FIG. 5, and in another embodiment, the disclosure provides an insertion tool 80 having first elongate member 82 and second elongate member 84. The first elongate member 82 has a distal portion 85 with distal end 86, and likewise the second elongate member 84 has a distal portion 87 with distal end 88. The distal portion of each elongate member has an arcuate shape that provides the distal portion with a trough-like configuration. For example, the distal portion can have a configuration that resembles a half-diameter of a tube. The arcuate shape of the elongate member can be a portion of a circle or an oval, and can be about 180° or less, such as in the range of about 90° to about 180°. The same arcuate shape of the distal portion can extend proximally towards the proximal portion, or the arcuate shape can change towards the distal portion, for example the elongated member can flatten.

The first elongate member 82 also has a proximal portion 95 with tab 96, and likewise the second elongate member 84 has a proximal portion 97 with tab 98. Tabs 96 and 98 can be at an angle to the proximal portions of the elongate members. That is, the tab of an elongate portion can be directed away from the central cavity of the tool, such as an angle from about 30° to about 90° from the distal portion of the elongate member.

The insertion tool includes a set of hinges (i.e., first hinge 92 and second hinge 94) that attach the first elongate member 82 to the second elongate member 84. The hinges can be attached to inward protrusions (102, 104) from the first and second elongate members between the tab of the proximal portion, and the distal portion. The set of hinges can bias the distal ends of the first and second elongate members towards each other. For example, the set of hinges can be a set of springs or coils that maintains force between the distal ends of the first and second elongate members. The distal ends of the first and second elongate members can be moved apart by applying pressure to the tabs, such as by squeezing the tabs together. This results in the opening of the distal end of the insertion tool and can provide a passageway from the proximal end, between the tabs, to the distal end.

Figure 6:
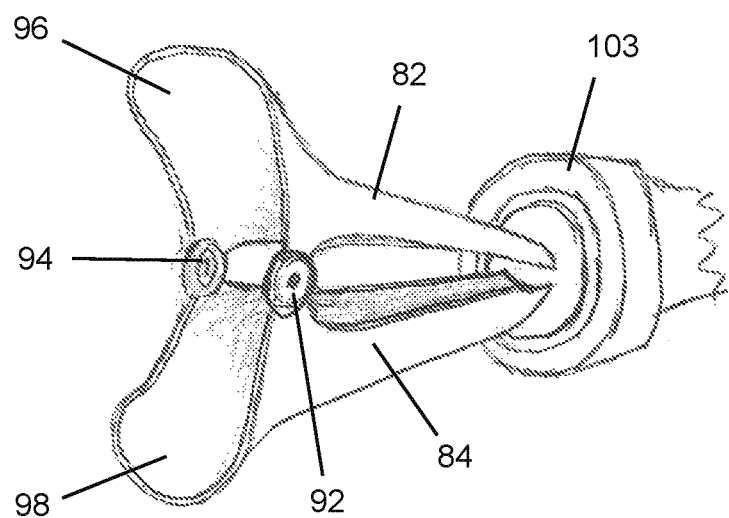
FIG. 6 is an illustration of an insertion tool according to one embodiment of the disclosure showing its proximal end along with a portion of a hemostatic valve.

For example, and with reference to FIG. 6, in a method of using the distal ends of the first and second elongate members of the insertion tool can be placed within an opening of a hemostatic valve 103, such as a silicone valve. The tabs 96 and 98 can be depressed, causing the distal ends to spread apart, and forcing the material of the valve to widen. At this point, the distal end of a balloon catheter can be moved through the inner portion of the insertion tool, from the proximal end, though the distal portion, and into the hemostatic valve 103.

Figure 7A:
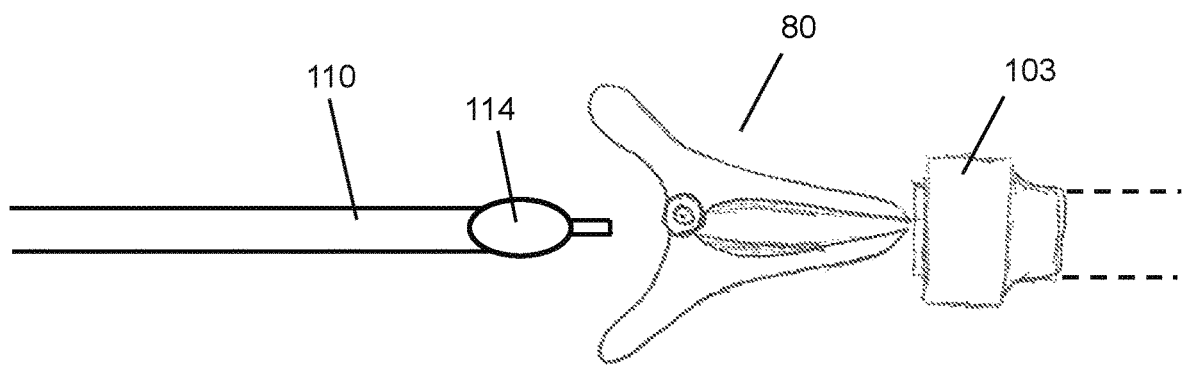
FIGS. 7a-7c are illustrations of an insertion tool according to one embodiment of the disclosure, along with a hemostatic valve and a portion of a balloon catheter.
Figure 7B:
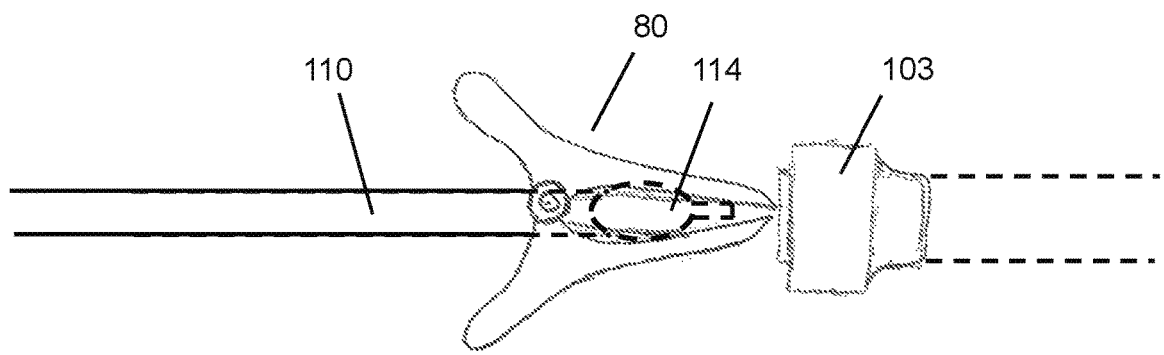
Figure 7C:
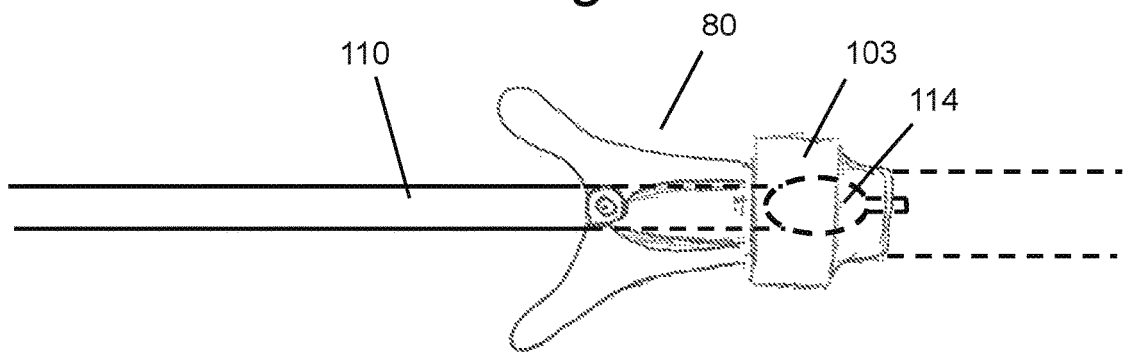

FIG. 7a shows a balloon catheter 110 with balloon portion 114, the insertion tool 80, and a hemostatic valve 103 on an artery. Referring to FIG. 7b, the balloon end 112 is advanced proximally into the insertion tool between the distal portions of the first elongate member 82 and second elongate member 84. Next, referring to FIG. 7c, the distal end of the insertion tool 80 is inserted into an opening of a hemostatic valve 103, and then the distal ends of the first and second elongate members are moved apart in the valve 103 by applying pressure to the tabs, causing the opening of the valve to widen, allowing easy entry of the balloon end 112 of the balloon catheter 110.

Figure 8A:
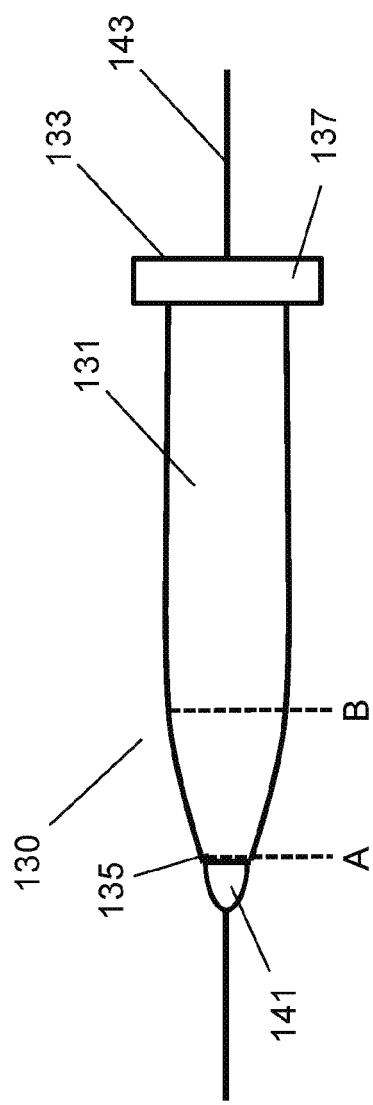
FIGS. 8a-8d are illustrations of an insertion tool with a locking mechanism, and portions thereof, according to one embodiment of the disclosure, along with a portion of a balloon catheter.
Figure 8D:
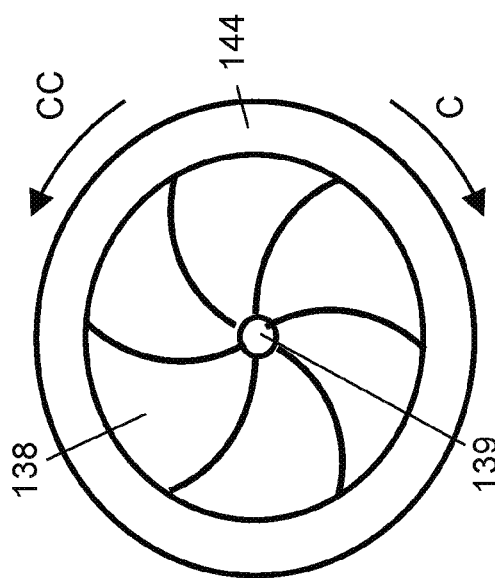
Figure 8C:
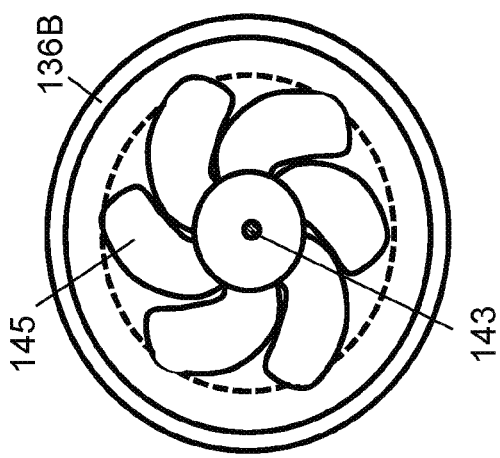
Figure 8B:
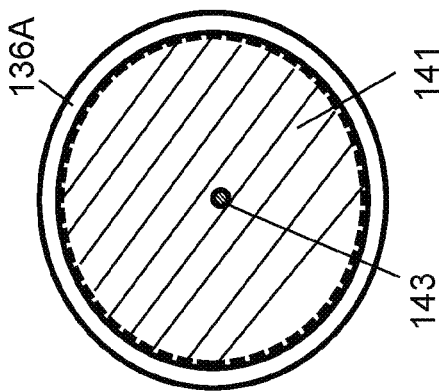

With reference to FIGS. 8a-8c, and in another embodiment, the disclosure provides an insertion tool 130 having an elongate hollow body 131 having a proximal end 133 and distal end 135. The elongate hollow body is tapered at its distal end 135. For example, the diameter of the elongate hollow body 131 can decrease over a portion of its length to provide a distal end 135 with an opening that can allow passage of a balloon portion of a balloon catheter in a folded uninflated state 145. In exemplary designs, the proximal portion of the elongate hollow body 131 has an outer diameter in the range of about 2.4 cm to about 2.7 cm, which then tapers towards the distal end 135 which has an outer diameter in the range of about 2.2 cm to about 2.4 cm. The insertion tool 130 also can include a locking mechanism 137 located at the proximal end of the elongate hollow body 131.

FIG. 8a shows the insertion tool 130 and portions of a balloon catheter that are the guidewire 143 and the distal tip 141 of the balloon. The balloon catheter is held in place within the elongate hollow body 131. A balloon catheter can be supplied to a user with the balloon catheter mounted in the insertion tool 130, or the insertion tool can be provided separately from the balloon catheter, and the balloon catheter mounted prior to the insertion procedure.

The distal portion of the insertion tool 130 can be tapered towards its distal end. The opening at the distal end can be sized to fit the tip of the balloon, which can position and stabilize the balloon catheter along the central axis of the elongate hollow body 131.

FIG. 8b is a cross-sectional illustration of insertion tool 130 at plane "A" (with reference to FIG. 8A), showing the distal tip 141 of the balloon catheter loaded in the elongate hollow body 131 viewed from the distal end of the tool. The balloon tip 141 and guidewire 143 are shown centered along a central axis, the central axis within and extending from the distal to proximal end of the elongate hollow body 131.

FIG. 8c is a cross-sectional illustration of insertion tool 130 at plane "B" (with reference to FIG. 8A), showing the balloon catheter loaded in the elongate hollow body 131 at viewed from proximal end of the tool. The balloon portion of the balloon catheter is shown in an uninflated folded configuration, including multiple flaps 145 of the balloon folded on each other in a circumferential manner. At least at this location, the outermost portion of the flaps 145 of the balloon that are furthest from the central axis (e.g., guidewire 143) are spaced away from the inner surface of the wall 136 of the elongate hollow body 131.

The locking mechanism 137 can be mechanically actuated to apply pressure to a part of the balloon catheter along its length (such as a portion, like the guidewire, that is proximal to the balloon portion) to secure the balloon catheter within the insertion tool 130. Securing the balloon catheter can prevent its movement relative to the elongate hollow body in a proximal to distal direction, and can accordingly maintain the balloon portion of the catheter centered within the hollow elongate body during an insertion procedure.

An exemplary locking mechanism is shown in FIG. 8d, which is a view of the insertion tool 130 from its proximal end. The locking mechanism 137 is attached to the proximal end of the elongate hollow body 131. In one arrangement the locking mechanism 137 includes a ring 144 that is rotatable in clockwise (C) and counterclockwise (CC) directions to tighten and loosen the locking mechanism 137. Within the ring 144 can be a diaphragm-type of valve (e.g., an iris valve) that provides an opening 139 in the center of the locking mechanism through which a portion of the balloon catheter (not shown) can be placed. The size of the opening 139 can be changed by rotation of the ring, which causes movement of leaves 138. For example, the guidewire can be placed through the opening 139, and then the ring 144 can be rotated in direction C to cause leaves 138 of the valve to move, contact, and apply pressure to the circumference of the outer surface of the guidewire (not shown), thereby securing the balloon catheter.

Figure 9:
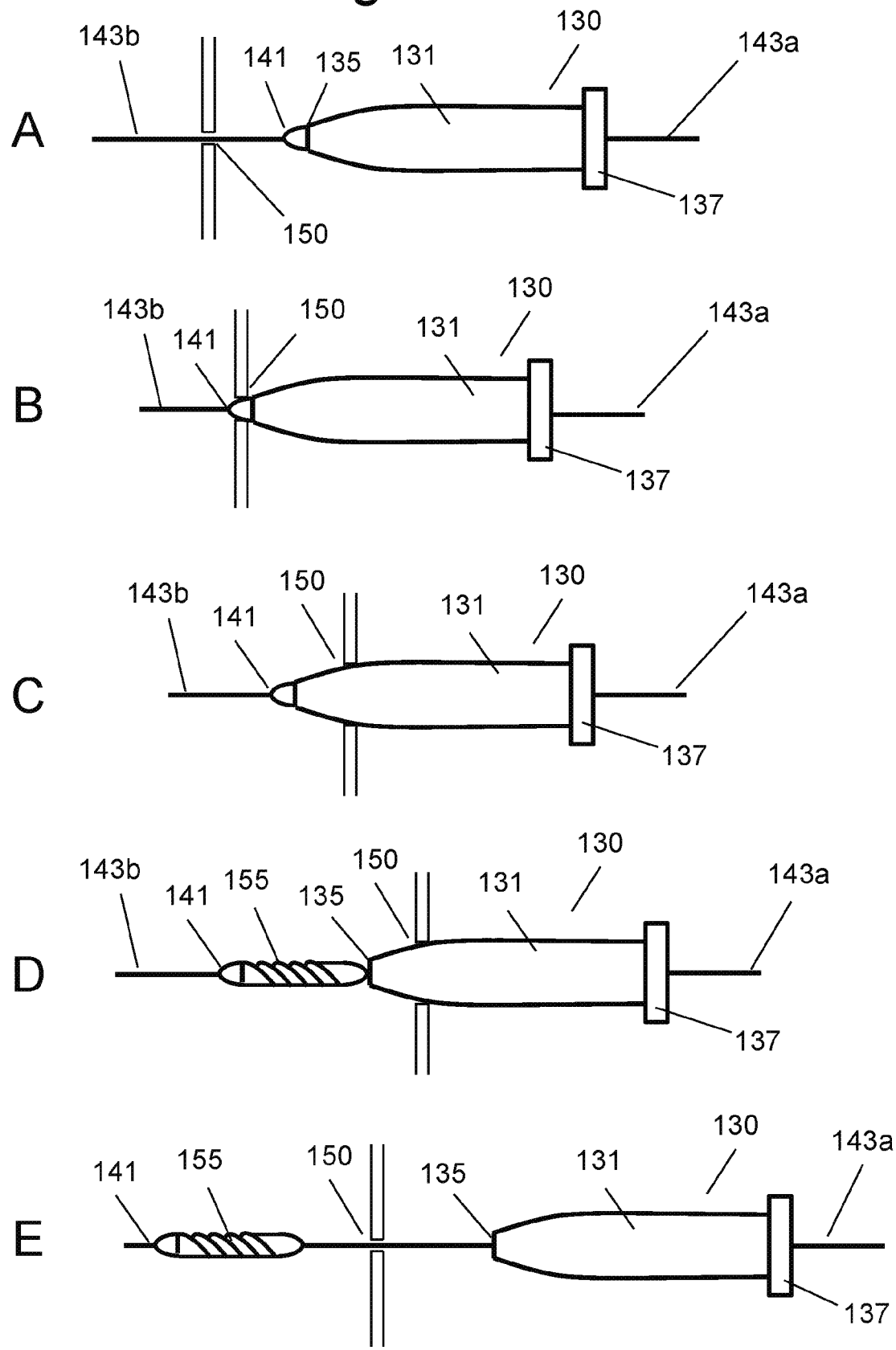
FIGS. 9a-9e are illustrations of a method of inserting a balloon catheter using an insertion tool with a locking mechanism, according to one embodiment of the disclosure

Exemplary steps of a method of inserting a balloon catheter using the insertion tool 130 are shown in FIGS. 9A-9E. FIG. 9A shows the insertion tool 130 with a balloon portion of a balloon catheter (not shown) disposed and secured within the elongate hollow body. Shown are the proximal 143a and distal ends 143b of the guidewire, and the distal tip 141 of the balloon portion of the catheter, which extends distally beyond the distal end 135 of the elongate hollow body. The distal portion 143b of the guidewire is shown as disposed through an insertion site 150 and within a patient. The locking mechanism 137 can be in a locked position which causes movement of the entire balloon catheter, including the guidewire and balloon portion, when the insertion tool is moved. FIG. 9B shows that the insertion tool 130 is moved to provide the tip 141 of the balloon portion (not shown) of the balloon catheter in the insertion site 150. FIG. 9C shows that the distal tapered end 149 of the insertion tool 130 is continued to advance through the insertion site 150, which can widen the insertion site while protecting the balloon from contact with the insertion site 150 as the device is advanced through this location. After at least a portion of the tapered end 149 is in the insertion site 150, the locking mechanism 137 is loosened. As a result, for example, the guidewire 143a can become unclamped and the entire balloon catheter can be allowed to move freely in relation to the insertion tool 130. FIG. 9D shows the balloon portion 155 of the balloon catheter can then be moved distally, out of the elongate hollow body 131 and beyond the distal end of the insertion tool 130. FIG. 9E shows the insertion tool 130 can then be moved in a proximal direction to withdraw it from the insertion site 150. The balloon portion 155 can then be advanced to the target site for performing treatment (e.g., balloon angioplasty).

Figure 11A:
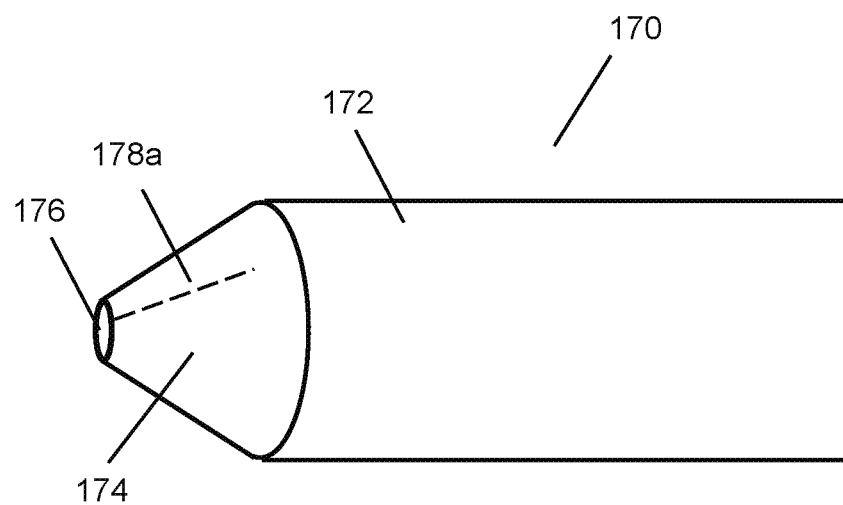
FIGS. 11a and 11b are illustrations of an insertion tool with a perforated tapered distal end, according to one embodiment of the disclosure, along with a portion of a balloon catheter.

Optionally, the insertion tool as show in FIGS. 8a-8d (optionally used according to the illustrations in FIGS. 9a-9e), can include one or more features according to features the insertion tools shown in FIGS. 10, 11a, and/or 11*b*. For example, the insertion tool with the locking mechanism can further include two or more elongate hollow bodies that are slidably disposed with one another, such as a first distal body having a tapered end that can hold the balloon tip, which can be slidable within a second proximal elongate hollow body having a locking mechanism at its proximal end. The distal tip of the insertion tool with the locking mechanism can also be configured to split apart upon application of force to provide a larger opening, and may include two or more perforations, slits, or thinned areas of the wall of the tapered distal end.

With reference to FIG. 10, and in another embodiment, the disclosure provides an insertion tool 160 having a first elongate hollow body 162 that is slidably movable within an inner diameter of a second elongate body 164. That is, the first and second bodies can provide a "telescoping"-like functionality, where the first body 162 can be partially or completely slid into the inner diameter of the second body 164. Although two elongate hollow bodies are shown, the insertion tool can include one or more additional elongate hollow bodies which can be slidably movable in relation to the first and second bodies. The first hollow body 162 includes an opening 165 sized to accommodate and allow the passage of a balloon portion 167 of a balloon catheter when the balloon portion 167 is in a folded uninflated state. The first elongate hollow body 162 may also have a tapered distal end for ease of insertion.

Insertion tool 160 can be used in a method for introducing a balloon catheter into a patient's body, where the balloon catheter is initially disposed within the first elongate hollow body. In the method, the insertion tool 160 with the balloon portion of a balloon catheter loaded into the first elongate hollow body. The distal end of the first elongate hollow body is introduced in the patient's body, and then the balloon catheter is moved distally out of the first elongate hollow body into the patient. The first elongate hollow body is them moved proximally out of the patient's body. At one or more points during the method the first elongate hollow body is moved in relation to the second elongate hollow body. For example, prior to introducing the distal end into the patient, the first elongate hollow body can be fully or partially disposed within the second elongate body, and then upon introduction of the distal end, the first elongate hollow body is moved distally out of the second elongate hollow body. After the distal end of the first elongate hollow body is within the patient, it may be moved proximally and into the second elongate hollow body to expose the balloon portion of the balloon catheter in the patient. The first elongate hollow body many also be moved proximally and into the second elongate hollow body to completely withdraw the distal end of the first elongate hollow body from the patient. Once delivery of the balloon portion 167 is complete, the elongate hollow bodies 162, 164 can be slidably collapsed (telescoped) and removed proximally to the insertion device. One advantage of the collapsed hollow bodies 162, 164 can be that the insertion tool 160 occupies less space proximally on the medical device, allowing for less encumbered activities by the medical professional.

Optionally, the insertion tool as show in FIG. 10 can include one or more features according to features the insertion tools shown in FIGS. 8*a*-8*d*, 11*a*, and/or 11*b*. For example, the insertion tool with the telescoping mechanism can further include a locking mechanism, such as shown in FIG. 8*d*, at the proximal end of the second elongate hollow body. The insertion tool with the telescoping mechanism can further include a distal tip on the distal end of the first elongate hollow body configured to split apart upon application of force to provide a larger opening, and may include two or more perforations, slits, or thinned areas of the wall of the tapered distal end.

In some embodiments, the insertion tool has a tapered distal end that is able to be split open upon application of force to provide an opening of a greater size that facilitates movement of the balloon portion of the balloon catheter out of the distal end. The distal tip can be prepared to provide one or more areas of material weakness which can facilitate the splitting of the distal tip. For example, these areas may include perforations, slits, or thinned areas of the wall of the tapered distal end.

As an example and with reference to FIG. 11*a*, in this embodiment of the disclosure an insertion tool 170 having an elongate hollow body 172 comprising a tapered distal end 174 comprising an opening 176 and two or more perforations (178*a*, 178*b* not shown) is provided. The tapered end can be split open along the perforations to increase the size of the opening and allow for passage of a balloon catheter.

Figure 11B:
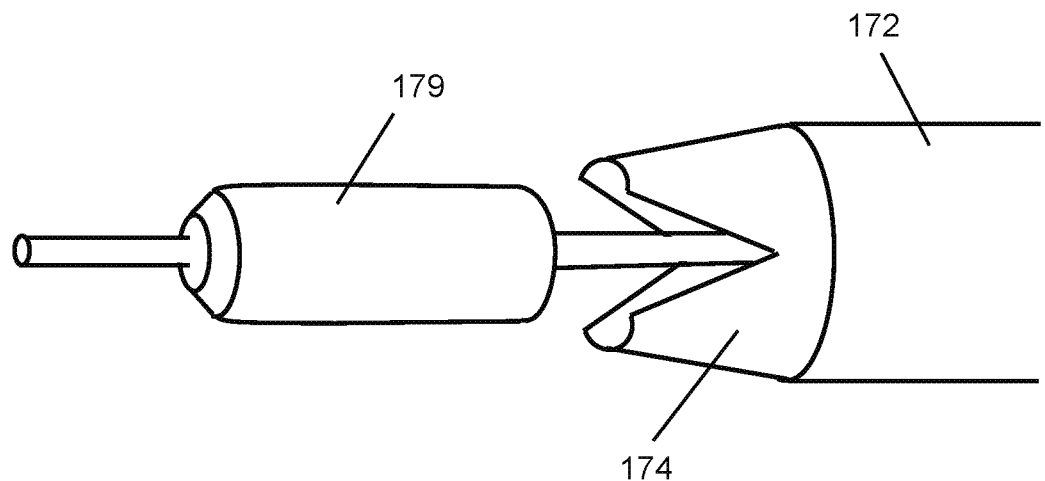

For example, in a method for introducing a balloon catheter into a patient's body, the insertion tool 170 is first provided with the elongate hollow body 172 housing a balloon portion of a balloon catheter. The tapered distal end 174 of the elongate hollow body is introduced into the patient's body. With reference to FIG. 11*b*, the tapered end is forced to be split open along the perforations to increase the size of the opening and allow for passage of a balloon catheter 179 which can be moved distally out of the opening at the split distal end.

Optionally, the insertion tool as show in FIGS. 11*a* and 11*b* can include one or more features according to features the insertion tools shown in FIGS. 8*a*-8*d*, and 10. For example, the insertion tool with the tapered distal end with one or more areas of weakness can include a locking mechanism, such as shown in FIG. 8*d*, at the proximal end of the elongate hollow body. As another example, the insertion tool with the tapered distal end with one or more areas of weakness can further include two or more elongate hollow bodies that are slidably disposed with one another, such as a first distal body having a tapered end, which can be slidable within a second proximal elongate hollow body.

Figure 12A:
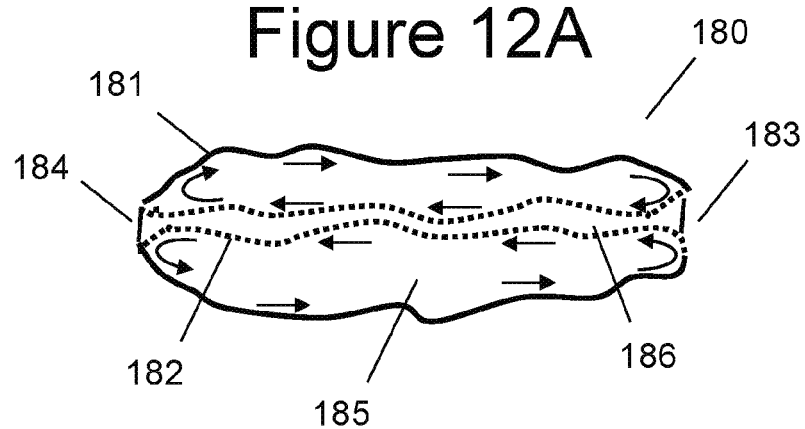
FIGS. 12a-c are illustrations of an insertion article according to one embodiment of the disclosure, along with a portion of a balloon catheter.

In another embodiment, the disclosure provides an insertion article for facilitating the entry of a balloon catheter into the body, wherein the insertion article is formed of a pliable material having interior and exterior surfaces that are continuous with each other and that can be moved around a liquid or gel 185 that is encompassed by the pliable material. An example of the insertion article is shown in FIG. 12*a*, which is a cross-sectional view of the tubular article 180 with outer surface 181 and inner surface 182. The inner surface 182 defines a cavity 186 between the proximal 183 and distal ends 184 of the article.

The article generally has an elongate tubular shape, but the shape is not dimensionally fixed because the article is formed of pliable material, such as a thin plastic material that surrounds a liquid or gel center. Because of its tubular shape and continuous surface, the outer and inner surfaces are able to be moved around the liquid or gel while the article is stationary. FIG. 12A shows that the pliable material can be pulled on its outer surface in a proximal direction, and then pushed on its inner surface in a distal direction to affect movement of the pliable material according to the arrows. An object placed within the cavity can be moved in a proximal to distal direction when the pliable material forming the surfaces is moved in such a manner.

Figure 12B:
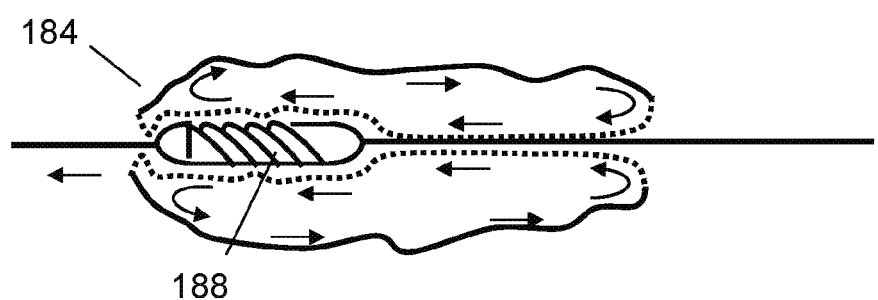
Figure 12C:
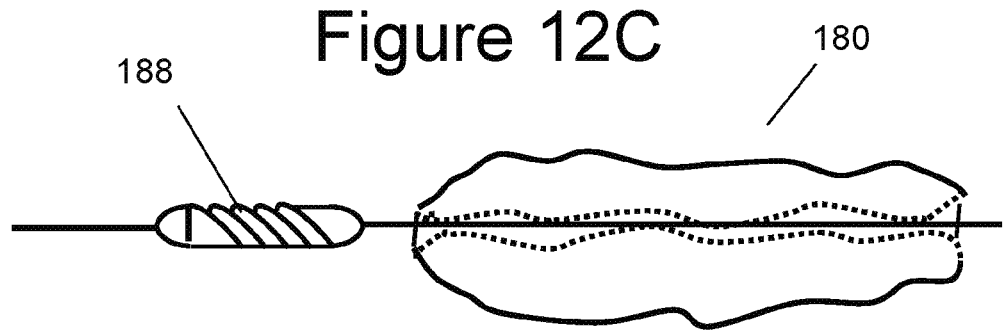

For example, as shown in FIG. 12B the balloon portion 188 of a balloon catheter can be positioned in the cavity 186 of the insertion article. The distal end of the insertion article can be placed at an insertion site. The pliable material can then be manipulated to affect movement of the pliable material according to the arrows, which in turn moves the balloon catheter in the distal direction. The balloon portion 188 of the balloon catheter enters the insertion site as shown the insertion article can then be withdrawn from the site, as shown in FIG. 12C.

In embodiments of the disclosure, any portion of any insertion tool/article, or any portions of catheter of the disclosure can have a coating, such as a hydrophilic lubricious coating. For example, hydrophilic polymeric base coatings can be applied to portions of the insertion tool/article, or any portions of catheter to impart lubricity and decrease particulate shedding. In some examples, portions of the valve on the distal end of the sleeve are covered with a coating. In other examples, the inner diameter of the sleeve is coated or lined with lubricious low friction coatings or the outer diameter is lined with lubricious low friction coatings, friction reducing or lubricating materials such as silicone oil, perfluorinated oils or waxes or with covalently bonded coating that imparts lower friction.

Exemplary embodiments of low friction surfaces for the vascular access devices described herein include substrates prepared from low friction materials (e.g. PTFE and PTFE liners) and surfaces that can be made to be low friction by addition of coatings (e.g. coatings with hydrophilic polymers).

One class of hydrophilic polymers useful as polymeric materials for hydrophilic base coat formation can be synthetic hydrophilic polymers. Synthetic hydrophilic polymers that are biostable (i.e., that show no appreciable degradation in vivo) can be prepared from any suitable monomer including acrylic monomers, vinyl monomers, ether monomers, or combinations of any one or more of these types of monomers. Acrylic monomers include, for example, methacrylate, methyl methacrylate, hydroxyethyl methacrylate, hydroxyethyl acrylate, methacrylic acid, acrylic acid, glycerol acrylate, glycerol methacrylate, acrylamide, methacrylamide, dimethylacrylamide (DMA), and derivatives and/or mixtures of any of these. Vinyl monomers include, for example, vinyl acetate, vinylpyrrolidone, vinyl alcohol, and derivatives of any of these. Ether monomers include, for example, ethylene oxide, propylene oxide, butylene oxide, and derivatives of any of these. Examples of polymers that can be formed from these monomers include poly(acrylamide), poly(methacrylamide), poly(vinylpyrrolidone), poly(acrylic acid), poly(ethylene glycol), poly(vinyl alcohol), and poly (HEMA). Examples of hydrophilic copolymers include, for example, methyl vinyl ether/maleic anhydride copolymers and vinyl pyrrolidone/(meth)acrylamide copolymers. Mixtures of homopolymers and/or copolymers can be used.

Examples of some acrylamide-based polymers, such as poly(N,Ndimethylacrylamide-co-aminopropylmethacrylamide) and poly(acrylamide-co-N,Ndimethylaminopropylmethacrylamide) are described in example 2 of U.S. Pat. No. 7,807,750 (Taton et al.), the disclosure of which is incorporated herein by reference.

Other hydrophilic polymers that can be useful in the present disclosure are derivatives of acrylamide polymers with photoreactive groups. One such representative hydrophilic polymer can be the copolymerization of N-[3-(4-benzoylbenzamido)propyl]methacrylamide (Formula I) with N-(3-aminopropyl)methacrylamide (Formula II) to produce the polymer poly(N-3-aminopropyl)methacrylamide-co-N-[3-(4-benzoylbenzamido)propyl]methacrylamide (Formula III). The preparation of the polymer is disclosed in Example 1 of US Patent Publication 2007/0032882 (to Lodhi, et al.), the full content of which is incorporated herein by reference.

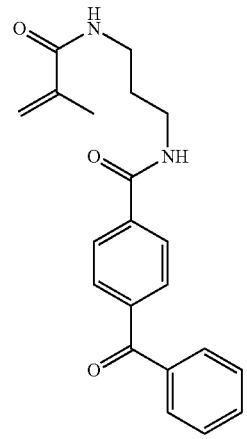

Formula I

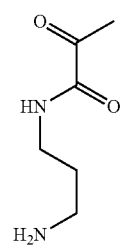

Formula II

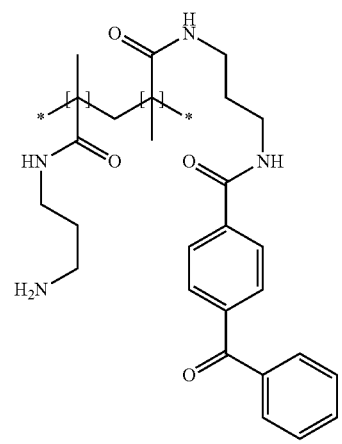

Formula III

In some embodiments, the hydrophilic polymer can be a vinyl pyrrolidone polymer, or a vinyl pyrrolidone/(meth) acrylamide copolymer such as poly(vinylpyrrolidone-co-methacrylamide). If a PVP copolymer is used, it can be a copolymer of vinylpyrrolidone and a monomer selected from the group of acrylamide monomers. Exemplary acrylamide monomers include (meth)acrylamide and (meth) acrylamide derivatives, such as alkyl(meth)acrylamide, as exemplified by dimethylacrylamide, and aminoalkyl(meth) acrylamide, as exemplified by aminopropylmethacrylamide and dimethylaminopropylmethacrylamide. For example, poly(vinylpyrrolidone-co-N,N-dimethylaminopropylmethacrylamide) is described in example 2 of U.S. Pat. No. 7,807,750 (Taton et al.).

In one embodiment, the polymers and copolymers as described are derivatized with one or more photoactivatable group(s). Exemplary photoreactive groups that can be pendent from biostable hydrophilic polymer include aryl ketones, such as acetophenone, benzophenone, anthraquinone, anthrone, quinone, and anthrone-like heterocycles. Aryl ketones herein can specifically include diaryl ketones. Polymers herein can provide a hydrophilic polymer having a pendent activatable photogroup that can be applied to the expandable and collapsible structure, and can then treated with actinic radiation sufficient to activate the photogroups and cause covalent bonding to a target, such as the material of the expandable and collapsible structure. Use of photohydrophilic polymers can be used to provide a durable coating of a flexible hydrogel matrix, with the hydrophilic polymeric materials covalently bonded to the material of the expandable and collapsible structure.

A hydrophilic polymer having pendent photoreactive groups can be used to prepare the flexible hydrogel coating. Methods of preparing hydrophilic polymers having photoreactive groups are known in the art. For example, methods for the preparation of photo-PVP are described in U.S. Pat. No. 5,414,075, the disclosure of which is incorporated herein by reference. Hydrophilic photo-polyacrylamide polymers such as poly(acrylamide-co-N-(3-(4-benzoylbenzamido)propyl) methacylamide), "Photo PA", and derivatives thereof can be used to form hydrophilic base coats in exemplary embodiments of the present disclosure. Methods for the preparation of photo-polyacrylamide are described in U.S. Pat. No. 6,007,833, the disclosure of which is incorporated herein by reference.

Other embodiments of hydrophilic base coats include derivatives of photo-polyacrylamide polymers incorporating additional reactive moieties. Some exemplary reactive moieties include N-oxysuccinimide and glycidyl methacrylate. Representative photo-polyacrylamide derivatives incorporating additional reactive moieties include poly(acrylamide-co-maleic-6-aminocaproic acid-N-oxysuccinimide-co-N-(3-(4-benzoylbenzamido)propyl)methacrylamide) and poly(acrylamide-co-(3-(4-benzoylbenzamido)propyl)methacrylamide)-co-glycidylmethacrylate. Additional photo-polyacrylamide polymers incorporating reactive moieties are described in U.S. Pat. No. 6,465,178 (to Chappa, et al.), U.S. Pat. No. 6,762,019 (to Swan, et al.) and U.S. Pat. No. 7,309,593 (to Ofstead, et al.), the disclosures of which are herein incorporated by reference.

Other embodiments of exemplary hydrophilic base coats that include derivatives of photo-polyacrylamide polymers incorporating additional reactive moieties can be found in U.S. Pat. No. 6,514,734 (to Clapper, et al.), the disclosure of which is incorporated herein by reference in its entirety.

In yet other embodiments, the hydrophilic base coat can include derivatives of photo-polyacrylamide polymers incorporating charged moieties. Charged moieties include both positively and negatively charged species. Exemplary charged species include, but are not limited to, sulfonates, phosphates and quaternary amine derivatives. Some examples include the negatively charged species N-acetylated poly(acrylamide-co-sodium-2-acrylamido-2-methylpropanesulfonate-co-N-(3-(4-benzoylbenzamido)propyl) methacrylamide)-co-methoxy poly(ethylene glycol) monomethacrylate. Other negatively charged species that can be incorporated into the hydrophilic base coat are described in U.S. Pat. No. 4,973,993, the disclosure of which is incorporated herein by reference in its entirety. Positively charged species can include poly(acrylamide-co-N-(3-(4-benzoylbenzamido)propyl)methacrylamide)-co-(3-(methacryloylamino)propyl)trimethylammonium chloride. Other positively charged species that can be incorporated into the hydrophilic base coat are described in U.S. Pat. No. 5,858,653 (to Duran et al.), the disclosure of which is incorporated herein by reference in its entirety.

In another embodiment, the polymers and copolymers as described are derivatized with one or more polymerizable group(s). Polymers with pendent polymerizable groups are commonly referred to as macromers. The polymerizable group(s) can be present at the terminal portions (ends) of the polymeric strand or can be present along the length of the polymer. In one embodiment polymerizable groups are located randomly along the length of the polymer.

Exemplary hydrophilic polymer coatings can be prepared using polymer grafting techniques. Polymer grafting techniques can include applying a nonpolymeric grafting agent and monomers to a substrate surface then causing polymerization of the monomers on the substrate surface upon appropriate activation (for example, but not limited to, UV radiation) of the grafting agent. Grafting methods producing hydrophilic polymeric surfaces are exemplified in U.S. Pat. Nos. 7,348,055; 7,736,689 and 8,039,524 (all to Chappa et al.) the full disclosures of which are incorporated herein by reference.

Optionally, the coating can include a crosslinking agent. A crosslinking agent can promote the association of polymers in the coating, or the bonding of polymers to the coated surface. The choice of a particular crosslinking agent can depend on the ingredients of the coating composition.

Suitable crosslinking agents can include two or more activatable groups, which can react with the polymers in the composition. Suitable activatable groups can include photoreactive groups as described herein, like aryl ketones, such as acetophenone, benzophenone, anthraquinone, anthrone, quinone, and anthrone-like heterocycles. A crosslinking agent including a photoreactive group can be referred to as a photo-crosslinker or photoactivatable crosslinking agent. The photoactivatable crosslinking agent can be ionic, and can have good solubility in an aqueous composition. Thus, in some embodiments, at least one ionic photoactivatable crosslinking agent can be used to form the coating. The ionic crosslinking agent can include an acidic group or salt thereof, such as selected from sulfonic acids, carboxylic acids, phosphonic acids, salts thereof, and the like. Exemplary counter ions include alkali, alkaline earths metals, ammonium, protonated amines, and the like.

Exemplary ionic photoactivatable crosslinking agents include 4,5-bis(4-benzoylphenylmethyleneoxy) benzene-1,3-disulfonic acid or salt; 2,5-bis(4-benzoylphenylmethyleneoxy)benzene-1,4-disulfonic acid or salt; 2,5-bis(4-benzoylmethyleneoxy)benzene-1-sulfonic acid or salt; N,N-bis[2-(4-benzoylbenzyloxy)ethyl]-2-aminoethanesulfonic acid or salt, and the like. See U.S. Pat. No. 6,077,698 (Swan et al.), U.S. Pat. No. 6,278,018 (Swan), U.S. Pat. No. 6,603,040 (Swan) and U.S. Pat. No. 7,138,541 (Swan) the disclosures of which are incorporated herein by reference.

Other exemplary ionic photoactivatable crosslinking agents include ethylenebis(4-benzoylbenzyldimethylammonium) dibromide and hexamethylenebis(4-benzoylbenzyldimethylammonium) dibromide and the like. See U.S. Pat. No. 5,714,360 (Swan et al.) the disclosures of which are incorporated herein by reference.

In yet other embodiments, restrained multifunctional reagents with photoactivable crosslinking groups can be used. In some examples these restrained multifunctional reagents include tetrakis (4-benzoylbenzyl ether) of pentaerthyritol and the tetrakis (4-benzoylbenzoate ester) of pentaerthyritol. See U.S. Pat. No. 5,414,075 (Swan et al.) and U.S. Pat. No. 5,637,460 (Swan et al.) the disclosures of which are incorporated herein by reference.

Additional crosslinking agents can include those having formula Photo1-LG-Photo2, wherein Photo1 and Photo2 independently represent at least one photoreactive group and LG represents a linking group comprising at least one silicon or at least one phosphorus atom, wherein the degradable linking agent comprises a covalent linkage between at least one photoreactive group and the linking group, wherein the covalent linkage between at least one photoreactive group and the linking group is interrupted by at least one heteroatom. See U.S. Pat. No. 8,889,760 (Kurdyumov, et al.), the disclosure of which is incorporated herein by reference. Further crosslinking agents can include those having a core molecule with one or more charged groups and one or more photoreactive groups covalently attached to the core molecule by one or more degradable linkers. See U.S. Publ. Pat. App. No. 2011/0144373 (Swan, et al.), the disclosure of which is incorporated herein by reference.

Crosslinking agents used in accordance with embodiments herein can include those with at least two photoreactive groups. Exemplary crosslinking agents are described in U.S. Pat. No. 8,889,760, the content of which is herein incorporated by reference in its entirety.

In some embodiments, the first and/or second crosslinking agent can have a molecular weight of less than about 1500 kDa. In some embodiments the crosslinking agent can have a molecular weight of less than about 1200, 1100, 1000, 900, 800, 700, 600, 500, or 400.

In some embodiments, at least one of the first and second crosslinking agents comprising a linking agent having formula Photo1-LG-Photo2, wherein Photo1 and Photo2, independently represent at least one photoreactive group and LG represents a linking group comprising at least one silicon or at least one phosphorus atom, there is a covalent linkage between at least one photoreactive group and the linking group, wherein the covalent linkage between at least one photoreactive group and the linking group is interrupted by at least one heteroatom.

In some embodiments, at least one of the first and second crosslinking agents comprising a linking agent having a formula selected from:

(a)

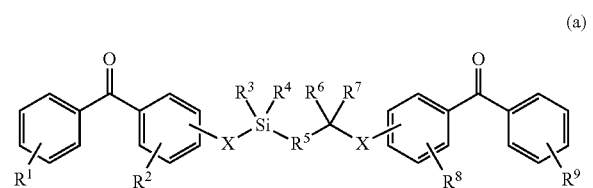

wherein R1, R2, R8 and R9 are any substitution; R3, R4, R6 and R7 are alkyl, aryl, or a combination thereof; R5 is any substitution; and each X, independently, is O, N, Se, S, or alkyl, or a combination thereof;

(b)

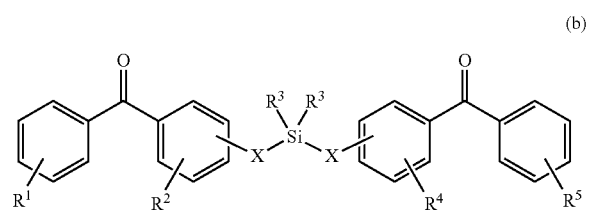

wherein R1 and R5 are any substitution; R2 and R4 can be any substitution, except OH; R3 can be alkyl, aryl, or a combination thereof; and X, independently, are O, N, Se, S, alkylene, or a combination thereof;

(c)

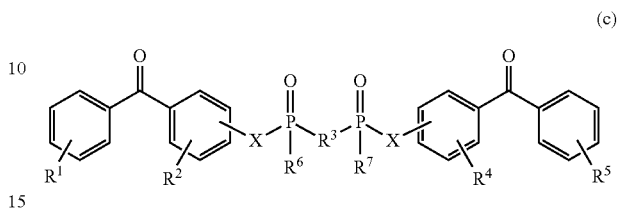

wherein R1, R2, R4 and R5 are any substitution; R3 is any substitution; R6 and R7 are alkyl, aryl, or a combination thereof; and each X can independently be O, N, Se, S, alkylene, or a combination thereof; and (d)

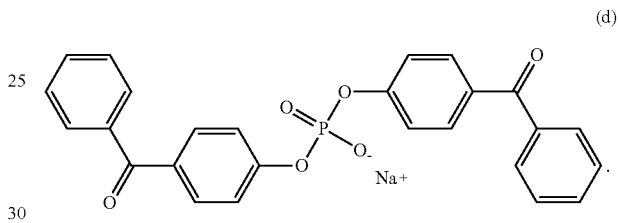

In a particular embodiment, the crosslinking agent can be bis(4-benzoylphenyl) phosphate.

In some embodiments, the photoactivatable crosslinking agent can be ionic, and can have good solubility in an aqueous composition, such as the first and/or second coating composition. Thus, in some embodiments, at least one ionic photoactivatable crosslinking agent is used to form the coating. In some cases, an ionic photoactivatable crosslinking agent can crosslink the polymers within the second coating layer which can also improve the durability of the coating.

Any suitable ionic photoactivatable crosslinking agent can be used. In some embodiments, the ionic photoactivatable crosslinking agent is a compound of formula I: X1-Y-X2 where Y is a radical containing at least one acidic group, basic group, or a salt of an acidic group or basic group. X1 and X2 are each independently a radical containing a latent photoreactive group. The photoreactive groups can be the same as those described herein. Spacers can also be part of X1 or X2 along with the latent photoreactive group. In some embodiments, the latent photoreactive group includes an aryl ketone or a quinone.

The radical Y in formula I provides the desired water solubility for the ionic photoactivatable crosslinking agent. The water solubility (at room temperature and optimal pH) is at least about 0.05 mg/ml. In some embodiments, the solubility is about 0.1 to about 10 mg/ml or about 1 to about 5 mg/ml.

In some embodiments of formula I, Y is a radical containing at least one acidic group or salt thereof. Such a photoactivatable crosslinking agent can be anionic depending upon the pH of the coating composition. Suitable acidic groups include, for example, sulfonic acids, carboxylic acids, phosphonic acids, and the like. Suitable salts of such groups include, for example, sulfonate, carboxylate, and phosphate salts. In some embodiments, the ionic crosslinking agent includes a sulfonic acid or sulfonate group. Suitable counter ions include alkali, alkaline earths metals, ammonium, protonated amines, and the like.

For example, a compound of formula I can have a radical Y that contains a sulfonic acid or sulfonate group; X1 and X2 can contain photoreactive groups such as aryl ketones. Such compounds include 4,5-bis(4-benzoylphenylmethyleneoxy) benzene-1,3-disulfonic acid or salt; 2,5-bis(4-benzoylphenylmethyleneoxy)benzene-1,4-disulfonic acid or salt; 2,5-bis(4-benzoylmethyleneoxy)benzene-1-sulfonic acid or salt; N,N-bis[2-(4-benzoylbenzyloxy)ethyl]-2-aminoethanesulfonic acid or salt, and the like. See U.S. Pat. No. 6,278,018. The counter ion of the salt can be, for example, ammonium or an alkali metal such as sodium, potassium, or lithium.

In other embodiments of formula I, Y can be a radical that contains a basic group or a salt thereof. Such Y radicals can include, for example, an ammonium, a phosphonium, or a sulfonium group. The group can be neutral or positively charged, depending upon the pH of the coating composition. In some embodiments, the radical Y includes an ammonium group. Suitable counter ions include, for example, carboxylates, halides, sulfate, and phosphate. For example, compounds of formula I can have a Y radical that contains an ammonium group; X1 and X2 can contain photoreactive groups that include aryl ketones. Such photoactivatable crosslinking agents include ethylenebis(4-benzoylbenzyldimethylammonium) salt; hexamethylenebis (4-benzoylbenzyldimethylammonium) salt; 1,4-bis(4-benzoylbenzyl)-1,4-dimethylpiperazinediium) salt, bis(4-benzoylbenzyl) hexamethylenetetraminediium salt, bis[2,-(4-benzoylbenzyldimethylammonio) ethyl]-4-benzoylbenzylmethylammonium salt; 4,4-bis(4-benzoylbenzyl)morpholinium salt; ethylenebis[(2-(4-benzoylbenzyldimethylammonio)ethyl)-4-benzoylbenzylmethylammonium]salt; and 1,1,4,4-tetrakis (4-benzoylbenzyl)piperzinediium salt. See U.S. Pat. No. 5,714,360. The counter ion is typically a carboxylate ion or a halide. On one embodiment, the halide is bromide.

In other embodiments, the ionic photoactivatable crosslinking agent can be a compound having the formula:

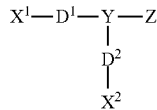

wherein X1 includes a first photoreactive group; X2 includes a second photoreactive group; Y includes a core molecule; Z includes at least one charged group; D1 includes a first degradable linker; and D2 includes a second degradable linker. Additional exemplary degradable ionic photoactivatable crosslinking agents are described in US Patent Application Publication US 2011/0144373 (Swan et al., "Water Soluble Degradable Crosslinker"), the disclosure of which is incorporated herein by reference.

In some aspects a non-ionic photoactivatable crosslinking agent can be used. In one embodiment, the non-ionic photoactivatable crosslinking agent has the formula XR1R2R3R4, where X is a chemical backbone, and R1, R2, R3, and R4 are radicals that include a latent photoreactive group. Exemplary non-ionic crosslinking agents are described, for example, in U.S. Pat. Nos. 5,414,075 and 5,637,460 (Swan et al., "Restrained Multifunctional Reagent for Surface Modification"). Chemically, the first and second photoreactive groups, and respective spacers, can be the same or different.

In other embodiments, the non-ionic photoactivatable crosslinking agent can be represented by the formula:

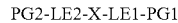

wherein PG1 and PG2 include, independently, one or more photoreactive groups, for example, an aryl ketone photoreactive group, including, but not limited to, aryl ketones such as acetophenone, benzophenone, anthraquinone, anthrone, anthrone-like heterocycles, their substituted derivatives or a combination thereof; LE1 and LE2 are, independently, linking elements, including, for example, segments that include urea, carbamate, or a combination thereof; and X represents a core molecule, which can be either polymeric or non-polymeric, including, but not limited to a hydrocarbon, including a hydrocarbon that is linear, branched, cyclic, or a combination thereof; aromatic, non-aromatic, or a combination thereof; monocyclic, polycyclic, carbocyclic, heterocyclic, or a combination thereof; benzene or a derivative thereof; or a combination thereof. Other non-ionic crosslinking agents are described, for example, in U.S. application Ser. No. 13/316,030 filed Dec. 9, 2011 (Publ. No. US 2012/0149934) (Kurdyumov, "Photocrosslinker"), the disclosure of which is incorporated herein by reference.

Further embodiments of non-ionic photoactivatable crosslinking agents can include, for example, those described in US Pat. Publication 2013/0143056 (Swan et al., "Photo-Vinyl Primers/Crosslinkers"), the disclosure of which is incorporated herein by reference. Exemplary crosslinking agents can include non-ionic photoactivatable crosslinking agents having the general formula R1-X-R2, wherein R1 is a radical comprising a vinyl group, X is a radical comprising from about one to about twenty carbon atoms, and R2 is a radical comprising a photoreactive group.

A single photoactivatable crosslinking agent or any combination of photoactivatable crosslinking agents can be used in forming the coating. In some embodiments, at least one nonionic crosslinking agent such as tetrakis(4-benzoylbenzyl ether) of pentaerythritol can be used with at least one ionic crosslinking agent. For example, at least one non-ionic photoactivatable crosslinking agent can be used with at least one cationic photoactivatable crosslinking agent such as an ethylenebis(4-benzoylbenzyldimethylammonium) salt or at least one anionic photoactivatable crosslinking agent such as 4,5-bis(4-benzoyl-phenylmethyleneoxy)benzene-1,3-disulfonic acid or salt. In another example, at least one nonionic crosslinking agent can be used with at least one cationic crosslinking agent and at least one anionic crosslinking agent. In yet another example, a least one cationic crosslinking agent can be used with at least one anionic crosslinking agent but without a non-ionic crosslinking agent.

An exemplary crosslinking agent is disodium 4,5-bis[(4-benzoylbenzyl)oxy]-1,3-benzenedisulfonate (DBDS). This reagent can be prepared by combining 4,5-Dihydroxylbenzyl-1,3-disulfonate (CHBDS) with 4-bromomethylbenzophenone (BMBP) in THF and sodium hydroxide, then refluxing and cooling the mixture followed by purification and recrystallization (also as described in U.S. Pat. No. 5,714,360, incorporated herein by reference).

Further crosslinking agents can include the crosslinking agents described in U.S. Publ. Pat. App. No. 2010/0274012 (to Guire et al.) and U.S. Pat. No. 7,772,393 (to Guire et al.) the content of all of which is herein incorporated by reference.

In some embodiments, crosslinking agents can include boron-containing linking agents including, but not limited to, the boron-containing linking agents disclosed in US Pat. Publication 2013/0302529 entitled "Boron-Containing Linking Agents" by Kurdyumov et al., the content of which is herein incorporated by reference. By way of example, linking agents can include borate, borazine, or boronate groups and coatings and devices that incorporate such linking agents, along with related methods. In an embodiment, the linking agent includes a compound having the structure (I):

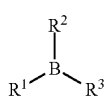
(I)

wherein R1 is a radical comprising a photoreactive group; R2 is selected from OH and a radical comprising a photoreactive group, an alkyl group and an aryl group; and R3 is selected from OH and a radical comprising a photoreactive group. In some embodiments the bonds B-R1, B-R2 and B-R3 can be chosen independently to be interrupted by a heteroatom, such as O, N, S, or mixtures thereof.

Additional agents for use with embodiments herein can include stilbene-based reactive compounds including, but not limited to, those disclosed in U.S. Pat. No. 8,487,137, entitled "Stilbene-Based Reactive Compounds, Polymeric Matrices Formed Therefrom, and Articles Visualizable by Fluorescence" by Kurdyumov et al., the content of which is herein incorporated by reference.

Additional photoreactive agents, crosslinking agents, hydrophilic coatings, and associated reagents are disclosed in U.S. Pat. No. 8,513,320 (to Rooijmans et al.); U.S. Pat. No. 8,809,411 (to Rooijmans); and 2010/0198168 (to Rooijmans), the content of all of which is herein incorporated by reference.

Natural polymers can also be used to form the hydrophilic base coat. Natural polymers include polysaccharides, for example, polydextrans, carboxymethylcellulose, and hydroxymethylcellulose; glycosaminoglycans, for example, hyaluronic acid; polypeptides, for example, soluble proteins such as collagen, albumin, and avidin; and combinations of these natural polymers. Combinations of natural and synthetic polymers can also be used.

In some instances a tie layer can be used to form the hydrophilic base layer. In yet other instances the tie layer can be added to the hydrophilic base layer. The tie layer can act to increase the adhesion of the hydrophilic base layer to the substrate. In other embodiments, the tie layer can act to increase adhesion of the hydrophobic active agent to the hydrophilic base layer. Exemplary ties layers include, but are not limited to silane, butadiene, polyurethane and parylene. Silane tie layers are described in US Patent Publication 2012/0148852 (to Jelle, et al.), the content of which is herein incorporated by reference.

In exemplary embodiments, the hydrophilic base layer can include tannic acid, polydopamine or other catechol containing materials.

The above detailed description is intended to be illustrative, and not restrictive. The scope of the disclosure should, therefore, be determined with references to the appended claims, along with the full scope of equivalents to which such claims are entitled.

What is claimed is:

1. An insertion tool for facilitating entry of a balloon catheter into a body, the tool comprising: first and second elongate hollow bodies comprising proximal and distal ends, wherein the proximal end of the first elongate hollow body has an outer diameter that is slidably movable within an inner diameter of the distal end of the second elongate hollow body, wherein the first elongate hollow body includes an opening sized to accommodate and allow passage of a balloon portion of a balloon catheter when the balloon portion is in a folded uninflated state, a locking mechanism at the proximal end of the second elongate hollow body, wherein the locking mechanism can be mechanically actuated to apply pressure to a part of the balloon catheter along its length to secure the balloon catheter within the insertion tool, wherein the locking mechanism comprises a diaphragm valve that provides an opening in a center of the locking mechanism through which a portion of the balloon catheter can be placed.

2. The insertion tool of claim 1, where the first elongate hollow body is capable of being partially slid into the inner diameter of the second elongate hollow body.

3. The insertion tool of claim 1, where the first elongate hollow body is capable of being completely slid into the inner diameter of the second elongate hollow body.

4. The insertion tool of claim 1, comprising one or more additional elongate hollow body or bodies slidably movable in relation to the first and second elongate bodies.

5. The insertion tool of claim 1 wherein the locking mechanism can be mechanically actuated to apply pressure to the part of the balloon catheter that is a guidewire.

6. The insertion tool of claim 1, wherein the distal end of the first elongate hollow body is tapered.

7. The insertion tool of claim 1, wherein the distal end of the first elongate hollow body is configured to split apart upon application of force to provide a larger opening at the distal end.

8. The insertion tool of claim 7, wherein the distal end of the first elongate hollow body comprises one or more perforations.

9. A method for facilitating entry of a balloon catheter into a body of a patient, the method comprising providing the insertion tool of claim 1 and a balloon catheter, wherein the balloon catheter is disposed within the first elongate hollow body of the insertion tool, introducing the distal end of the first elongate hollow body with the disposed balloon catheter into the body of the patient, moving the balloon catheter or first elongate hollow body so the balloon catheter is placed into the patient and distal to the distal end of the first elongate hollow body, and moving the first elongate hollow body proximally out of the body of the patient.

10. The method of claim 9 where, in introducing the distal end of the first elongate hollow body into the body of the patient, the first elongate hollow body is fully or partially disposed within the second elongate body.

11. The method of claim 10 further comprising moving a portion of the first elongate hollow body distally out of the second elongate hollow body.

12. The method of claim 11 wherein after the first elongate hollow body is moved distally out of the second elongate hollow body, a portion of the first elongate hollow body is moved proximally and into the second elongate hollow body to expose the balloon catheter in the patient.

13. The method of claim 9 wherein the insertion tool comprises the locking mechanism that applies pressure to a part of the balloon catheter along its length, and the locking mechanism is actuated to secure the balloon catheter within the insertion tool during introducing, and then actuated to unsecure the balloon catheter so the balloon catheter can be moved in relation to the first elongate hollow body.

14. The method of claim 9 further comprising a step of inflating the balloon catheter from an uninflated state to perform treatment at a target site.

15. The method of claim 14 wherein the balloon catheter comprises a drug coating.

* * * * *